US012569601B2

(12) United States Patent
Patil et al.

(10) Patent No.: US 12,569,601 B2
(45) Date of Patent: Mar. 10, 2026

(54) INCREASED OPERATIONAL CAPABILITIES OF A DIALYSIS SYSTEM

(71) Applicant: MOZARC MEDICAL US LLC, Minneapolis, MN (US)

(72) Inventors: Kaustubh R Patil, Plymouth, MN (US); Sukalyan Dutta, New Brighton, MN (US); Christopher M. Hobot, Rogers, MN (US); Bryant J. Pudil, Plymouth, MN (US)

(73) Assignee: MOZARC MEDICAL US LLC, Minneapolis, MN (US)

( * ) Notice: Subject to any disclaimer, the term of this patent is extended or adjusted under 35 U.S.C. 154(b) by 826 days.

(21) Appl. No.: 17/224,256

(22) Filed: Apr. 7, 2021

(65) Prior Publication Data

US 2022/0323661 A1     Oct. 13, 2022

(51) Int. Cl.
*A61M 1/16*          (2006.01)

(52) U.S. Cl.
CPC ........ *A61M 1/1647* (2014.02); *A61M 1/1611* (2014.02); *A61M 2205/3327* (2013.01); *A61M 2205/3334* (2013.01)

(58) Field of Classification Search
None
See application file for complete search history.

(56) References Cited

U.S. PATENT DOCUMENTS

| | | |
|---|---|---|
| 1,617,288 A | 2/1927 | Kenney |
| 2,703,313 A | 3/1955 | Gill |
| 3,608,729 A | 9/1971 | Haselden |
| 3,617,545 A | 11/1971 | Dubois |
| 3,617,558 A | 11/1971 | Jones |
| 3,669,878 A | 6/1972 | Marantz |
| 3,669,880 A | 6/1972 | Marantz |
| 3,776,819 A | 12/1973 | Williams |
| 3,850,835 A | 11/1974 | Marantz |
| 3,884,808 A | 5/1975 | Scott |
| 3,902,490 A | 9/1975 | Jacobsen |
| 3,989,622 A | 11/1976 | Marantz |
| 4,060,485 A | 11/1977 | Eaton |
| 4,073,725 A | 2/1978 | Takeuchi |
| 4,094,775 A | 6/1978 | Mueller |
| 4,142,845 A | 3/1979 | Lepp |
| 4,192,748 A | 3/1980 | Hyden |
| 4,206,054 A | 6/1980 | Moore |

(Continued)

FOREIGN PATENT DOCUMENTS

| | | |
|---|---|---|
| CN | 1487853 A | 4/2004 |
| CN | 102573618 | 7/2012 |

(Continued)

OTHER PUBLICATIONS

U.S. Appl. No. 13/757,693, filed Feb. 1, 2013, Medtronic.

(Continued)

*Primary Examiner* — Peter Keyworth

(57) ABSTRACT

The disclosure relates to systems and methods for increasing the functional capabilities of a sorbent-based dialysis system. The systems and methods allow for the mode of operation of the dialysis system to be switched between single pass mode and a sorbent based multi-pass mode by controlling an amount of water added to the dialysate between 0% to 100% of the dialysate flow rate.

18 Claims, 6 Drawing Sheets

(56) References Cited

U.S. PATENT DOCUMENTS

| | | | |
|---|---|---|---|
| 4,209,392 A | 6/1980 | Wallace |
| 4,269,708 A | 5/1981 | Bonomini |
| 4,371,385 A | 2/1983 | Johnson |
| 4,374,382 A | 2/1983 | Markowitz |
| 4,376,707 A | 3/1983 | Lehmann |
| 4,381,999 A | 5/1983 | Boucher |
| 4,460,555 A | 7/1984 | Thompson |
| 4,556,063 A | 12/1985 | Thompson |
| 4,562,751 A | 1/1986 | Nason |
| 4,581,141 A | 4/1986 | Ash |
| 4,612,122 A | 9/1986 | Ambrus |
| 4,650,587 A | 3/1987 | Polak |
| 4,661,246 A | 4/1987 | Ash |
| 4,678,408 A | 7/1987 | Mason |
| 4,684,460 A | 8/1987 | Issautier |
| 4,685,903 A | 8/1987 | Cable |
| 4,687,582 A | 8/1987 | Dixon |
| 4,750,494 A | 6/1988 | King |
| 4,765,907 A | 8/1988 | Scott |
| 4,826,663 A | 5/1989 | Alberti |
| 4,828,693 A | 5/1989 | Lindsay |
| 5,032,615 A | 7/1991 | Ward et al. |
| 5,047,014 A | 9/1991 | Mosebach et al. |
| 5,080,653 A | 1/1992 | Voss |
| 5,092,886 A | 3/1992 | Dobos-Hardy |
| 5,097,122 A | 3/1992 | Coiman |
| 5,127,404 A | 7/1992 | Wyborny |
| 5,192,132 A | 3/1993 | Pelensky |
| 5,230,702 A | 7/1993 | Lindsay |
| 5,284,470 A | 2/1994 | Beltz |
| 5,302,288 A | 4/1994 | Meidl |
| 5,305,745 A | 4/1994 | Zacouto |
| 5,308,315 A | 5/1994 | Khuri |
| 5,318,750 A | 6/1994 | Lascombes |
| 5,399,157 A | 3/1995 | Goux |
| 5,441,049 A | 8/1995 | Masano |
| 5,442,969 A | 8/1995 | Troutner |
| 5,445,610 A | 8/1995 | Evert |
| 5,468,388 A | 11/1995 | Goddard |
| 5,507,723 A | 4/1996 | Keshaviah |
| 5,662,806 A | 9/1997 | Keshaviah et al. |
| 5,683,432 A | 11/1997 | Goedeke |
| 5,685,988 A | 11/1997 | Malchesky |
| 5,716,400 A | 2/1998 | Davidson |
| 5,744,031 A | 4/1998 | Bene |
| 5,762,782 A | 6/1998 | Kenley |
| 5,770,086 A | 6/1998 | Indriksons |
| 5,849,179 A | 12/1998 | Emerson |
| 5,858,186 A | 1/1999 | Glass |
| 5,938,634 A | 8/1999 | Packard et al. |
| 5,938,938 A | 8/1999 | Bosetto |
| 5,944,684 A | 8/1999 | Roberts |
| 6,036,858 A | 3/2000 | Carlsson |
| 6,048,732 A | 4/2000 | Anslyn |
| 6,052,622 A | 4/2000 | Holmstrom |
| 6,058,331 A | 5/2000 | King |
| 6,114,176 A | 9/2000 | Edgson et al. |
| 6,126,831 A | 10/2000 | Goldau |
| 6,171,480 B1 | 1/2001 | Lee |
| 6,230,059 B1 | 5/2001 | Duffin |
| 6,248,093 B1 | 6/2001 | Moberg |
| 6,254,567 B1 | 7/2001 | Treu |
| 6,321,101 B1 | 11/2001 | Holmstrom |
| 6,362,591 B1 | 3/2002 | Moberg |
| 6,363,279 B1 | 3/2002 | Ben-Haim |
| 6,390,969 B1 | 5/2002 | Bolling et al. |
| 6,491,993 B1 | 12/2002 | Forbes |
| 6,521,184 B1 | 2/2003 | Edgson et al. |
| 6,554,798 B1 | 4/2003 | Mann et al. |
| 6,555,986 B2 | 4/2003 | Moberg |
| 6,565,525 B1 | 5/2003 | Burbank et al. |
| 6,572,769 B2 | 6/2003 | Rajan |
| 6,579,460 B1 | 6/2003 | Willis |
| 6,585,675 B1 | 7/2003 | O'Mahony et al. |
| 6,589,229 B1 | 7/2003 | Connelly |
| 6,593,747 B2 | 7/2003 | Puskas |
| 6,596,234 B1 | 7/2003 | Schnell et al. |
| 6,602,399 B1 | 8/2003 | Fromherz |
| 6,627,164 B1 | 9/2003 | Wong |
| 6,666,840 B1 | 12/2003 | Falkvall et al. |
| 6,676,608 B1 | 1/2004 | Keren |
| 6,695,807 B2 | 2/2004 | Bell et al. |
| 6,711,439 B1 | 3/2004 | Bradley |
| 6,719,745 B1 | 4/2004 | Taylor |
| 6,773,412 B2 | 8/2004 | O'Mahony et al. |
| 6,814,724 B2 | 11/2004 | Taylor |
| 6,818,196 B2 | 11/2004 | Wong |
| 6,861,266 B1 | 3/2005 | Sternby |
| 6,878,258 B2 | 4/2005 | Hughes |
| 6,878,283 B2 | 4/2005 | Thompson |
| 6,878,285 B2 | 4/2005 | Hughes |
| 6,890,315 B1 | 5/2005 | Levin |
| 6,923,782 B2 | 8/2005 | O'Mahony et al. |
| 6,960,179 B2 | 11/2005 | Gura |
| 7,029,456 B2 | 4/2006 | Ware et al. |
| 7,033,498 B2 | 4/2006 | Wong |
| 7,077,819 B1 | 7/2006 | Goldau |
| 7,097,630 B2 | 8/2006 | Gotch |
| 7,101,519 B2 | 9/2006 | Wong |
| 7,128,750 B1 | 10/2006 | Stergiopulos |
| 7,153,693 B2 | 12/2006 | Tajiri |
| 7,208,092 B2 | 4/2007 | Micheli |
| 7,241,272 B2 | 7/2007 | Karoor |
| 7,276,042 B2 | 10/2007 | Polaschegg |
| 7,309,323 B2 | 12/2007 | Gura |
| 7,318,892 B2 | 1/2008 | Connell |
| 7,326,576 B2 | 2/2008 | Womble et al. |
| 7,384,543 B2 | 6/2008 | Jonsson et al. |
| 7,435,342 B2 | 10/2008 | Tsukamoto |
| 7,462,161 B2 | 12/2008 | O'Mahony et al. |
| 7,488,447 B2 | 2/2009 | Sternby |
| 7,537,688 B2 | 5/2009 | Tarumi |
| 7,544,300 B2 | 6/2009 | Brugger |
| 7,544,737 B2 | 6/2009 | Poss |
| 7,563,240 B2 | 7/2009 | Gross |
| 7,566,432 B2 | 7/2009 | Wong |
| 7,575,564 B2 | 8/2009 | Childers |
| 7,597,806 B2 | 10/2009 | Uchi |
| 7,674,231 B2 | 3/2010 | Mccombie |
| 7,674,237 B2 | 3/2010 | O'Mahony et al. |
| 7,686,778 B2 | 3/2010 | Burbank et al. |
| 7,704,361 B2 | 4/2010 | Garde |
| 7,736,507 B2 | 6/2010 | Wong |
| 7,754,852 B2 | 7/2010 | Burnett |
| 7,756,572 B1 | 7/2010 | Fard |
| 7,776,001 B2 | 8/2010 | Brugger et al. |
| 7,776,006 B2 | 8/2010 | Childers |
| 7,776,210 B2 | 8/2010 | Rosenbaum |
| 7,794,141 B2 | 9/2010 | Perry |
| 7,794,419 B2 | 9/2010 | Paolini |
| 7,850,635 B2 | 12/2010 | Polaschegg |
| 7,867,214 B2 | 1/2011 | Childers |
| 7,901,376 B2 | 3/2011 | Steck et al. |
| 7,905,853 B2 | 3/2011 | Chapman et al. |
| 7,922,686 B2 | 4/2011 | Childers |
| 7,922,911 B2 | 4/2011 | Micheli |
| 7,947,179 B2 | 5/2011 | Rosenbaum |
| 7,955,289 B2 | 6/2011 | O'Mahony et al. |
| 7,955,290 B2 | 6/2011 | Karoor |
| 7,967,022 B2 | 6/2011 | Grant |
| 7,981,082 B2 | 7/2011 | Wang |
| 7,988,854 B2 | 8/2011 | Tsukamoto |
| 8,002,726 B2 | 8/2011 | Karoor |
| 8,012,118 B2 | 9/2011 | Curtin |
| 8,029,454 B2 | 10/2011 | Kelly |
| 8,034,161 B2 | 10/2011 | Gura |
| 8,066,658 B2 | 11/2011 | Karoor |
| 8,070,709 B2 | 12/2011 | Childers |
| 8,080,161 B2 | 12/2011 | Ding et al. |
| 8,087,303 B2 | 1/2012 | Beavis |
| 8,096,969 B2 | 1/2012 | Roberts |
| 8,180,574 B2 | 5/2012 | Lo |
| 8,182,673 B2 | 5/2012 | Childers et al. |
| 8,183,046 B2 | 5/2012 | Lu |

(56)  References Cited

U.S. PATENT DOCUMENTS

| | | | |
|---|---|---|---|
| 8,187,250 B2 | 5/2012 | Roberts |
| 8,197,439 B2 | 6/2012 | Wang |
| 8,206,591 B2 | 6/2012 | Kotanko et al. |
| 8,211,048 B2 | 7/2012 | Szamosfalvi et al. |
| 8,221,529 B2 | 7/2012 | Childers et al. |
| 8,226,595 B2 | 7/2012 | Childers et al. |
| 8,246,826 B2 | 8/2012 | Wilt |
| 8,267,881 B2 | 9/2012 | O'Mahony et al. |
| 8,273,049 B2 | 9/2012 | Demers |
| 8,292,594 B2 | 10/2012 | Tracey |
| 8,303,532 B2 | 11/2012 | Hamada |
| 8,313,642 B2 | 11/2012 | Yu |
| 8,317,492 B2 | 11/2012 | Demers |
| 8,357,113 B2 | 1/2013 | Childers |
| 8,357,298 B2 | 1/2013 | Demers et al. |
| 8,366,316 B2 | 2/2013 | Kamen |
| 8,366,655 B2 | 2/2013 | Kamen |
| 8,376,999 B2 | 2/2013 | Busby et al. |
| 8,377,012 B2 | 2/2013 | Chapman et al. |
| 8,377,308 B2 | 2/2013 | Kreymann et al. |
| 8,388,567 B2 | 3/2013 | Rovatti |
| 8,404,491 B2 | 3/2013 | Li |
| 8,409,441 B2 | 4/2013 | Wilt |
| 8,409,444 B2 | 4/2013 | Wong |
| 8,449,487 B2 | 5/2013 | Hovland et al. |
| 8,480,607 B2 | 7/2013 | Davies |
| 8,499,780 B2 | 8/2013 | Wilt |
| 8,518,260 B2 | 8/2013 | Raimann |
| 8,535,525 B2 | 9/2013 | Heyes |
| 8,580,112 B2 | 11/2013 | Updyke |
| 8,597,227 B2 | 12/2013 | Childers |
| 8,647,506 B2 | 2/2014 | Wong |
| 8,696,626 B2 | 4/2014 | Kirsch |
| 8,733,559 B2 | 5/2014 | Wong |
| 8,764,981 B2 | 7/2014 | Ding |
| 8,777,892 B2 | 7/2014 | Sandford |
| 8,903,492 B2 | 12/2014 | Soykan |
| 9,144,640 B2 | 9/2015 | Pudil |
| 9,254,355 B2 | 2/2016 | Sandford |
| 9,527,015 B2 | 12/2016 | Chau |
| 10,695,481 B2 | 6/2020 | Kelly |
| 2001/0007931 A1 | 7/2001 | Blatter |
| 2001/0009756 A1 | 7/2001 | Hei et al. |
| 2002/0016550 A1 | 2/2002 | Sweeney |
| 2002/0027106 A1 | 3/2002 | Smith |
| 2002/0042561 A1 | 4/2002 | Schulman |
| 2002/0062098 A1 | 5/2002 | Cavicchioli et al. |
| 2002/0112609 A1 | 8/2002 | Wong |
| 2002/0117436 A1 | 8/2002 | Rajan |
| 2003/0080059 A1 | 5/2003 | Peterson |
| 2003/0097086 A1 | 5/2003 | Gura |
| 2003/0105435 A1 | 6/2003 | Taylor |
| 2003/0113931 A1 | 6/2003 | Pan |
| 2003/0114787 A1 | 6/2003 | Gura |
| 2003/0138348 A1 | 7/2003 | Bell et al. |
| 2003/0187479 A1 | 10/2003 | Thong |
| 2004/0019312 A1 | 1/2004 | Childers |
| 2004/0019320 A1 | 1/2004 | Childers |
| 2004/0030277 A1 | 2/2004 | O'Mahony et al. |
| 2004/0037986 A1 | 2/2004 | Houston et al. |
| 2004/0054315 A1 | 3/2004 | Levin et al. |
| 2004/0082903 A1 | 4/2004 | Micheli |
| 2004/0084358 A1 | 5/2004 | O'Mahony et al. |
| 2004/0099593 A1 | 5/2004 | DePaolis |
| 2004/0147900 A1 | 7/2004 | Polaschegg |
| 2004/0168963 A1 | 9/2004 | King |
| 2004/0215090 A1 | 10/2004 | Erkkila |
| 2005/0006296 A1 | 1/2005 | Sullivan |
| 2005/0056592 A1 | 3/2005 | Braunger |
| 2005/0065760 A1 | 3/2005 | Murtfeldt |
| 2005/0101901 A1 | 5/2005 | Gura |
| 2005/0113796 A1 | 5/2005 | Taylor |
| 2005/0126961 A1 | 6/2005 | Bissler |
| 2005/0126998 A1 | 6/2005 | Childers |
| 2005/0131332 A1 | 6/2005 | Kelly |
| 2005/0148923 A1 | 7/2005 | Sternby |
| 2005/0150832 A1 | 7/2005 | Tsukamoto |
| 2005/0230313 A1 | 10/2005 | O'Mahony et al. |
| 2005/0234354 A1 | 10/2005 | Rowlandson |
| 2005/0234381 A1 | 10/2005 | Niemetz |
| 2005/0274658 A1 | 12/2005 | Rosenbaum |
| 2006/0025661 A1 | 2/2006 | Sweeney |
| 2006/0037483 A1 | 2/2006 | Kief |
| 2006/0157413 A1 | 7/2006 | Bene |
| 2006/0189926 A1 | 8/2006 | Hall et al. |
| 2006/0195064 A1 | 8/2006 | Plahey |
| 2006/0217771 A1 | 9/2006 | Soykan |
| 2006/0226079 A1 | 10/2006 | Mori |
| 2006/0241543 A1 | 10/2006 | Gura |
| 2006/0241709 A1 | 10/2006 | Soykan |
| 2006/0264894 A1 | 11/2006 | Moberg |
| 2007/0007208 A1 | 1/2007 | Brugger |
| 2007/0055296 A1 | 3/2007 | Stergiopulos |
| 2007/0066928 A1 | 3/2007 | Lannoy |
| 2007/0138011 A1 | 6/2007 | Hofmann |
| 2007/0175827 A1 | 8/2007 | Wariar |
| 2007/0179431 A1 | 8/2007 | Roberts et al. |
| 2007/0213665 A1 | 9/2007 | Curtin et al. |
| 2007/0215545 A1 | 9/2007 | Bissler |
| 2007/0243113 A1 | 10/2007 | DiLeo |
| 2007/0255250 A1 | 11/2007 | Moberg |
| 2008/0006570 A1 | 1/2008 | Gura |
| 2008/0011664 A1 | 1/2008 | Karoor |
| 2008/0015493 A1 | 1/2008 | Childers et al. |
| 2008/0021337 A1 | 1/2008 | Li |
| 2008/0051696 A1 | 2/2008 | Curtin |
| 2008/0053905 A9 | 3/2008 | Brugger |
| 2008/0067132 A1 | 3/2008 | Ross |
| 2008/0215247 A1 | 9/2008 | Tonelli |
| 2008/0217245 A1 | 9/2008 | Rambod |
| 2008/0241031 A1 | 10/2008 | Li |
| 2008/0292935 A1 | 11/2008 | Roelofs |
| 2009/0012864 A1 | 1/2009 | Goldberg |
| 2009/0020471 A1 | 1/2009 | Tsukamoto |
| 2009/0078636 A1 | 3/2009 | Uchi |
| 2009/0084199 A1 | 4/2009 | Wright |
| 2009/0101552 A1 | 4/2009 | Fulkerson |
| 2009/0101577 A1 | 4/2009 | Fulkerson |
| 2009/0120864 A1 | 5/2009 | Fulkerson |
| 2009/0127193 A1 | 5/2009 | Updyke |
| 2009/0149795 A1 | 6/2009 | O'Mahony et al. |
| 2009/0216045 A1 | 8/2009 | Singh |
| 2009/0266358 A1 | 10/2009 | Sacristan Rock |
| 2009/0275849 A1 | 11/2009 | Stewart |
| 2009/0275883 A1 | 11/2009 | Chapman |
| 2009/0281484 A1 | 11/2009 | Childers |
| 2009/0282980 A1 | 11/2009 | Gura |
| 2010/0004588 A1 | 1/2010 | Yeh |
| 2010/0007838 A1 | 1/2010 | Fujimoto |
| 2010/0010429 A1 | 1/2010 | Childers |
| 2010/0018923 A1 | 1/2010 | Rohde et al. |
| 2010/0030151 A1 | 2/2010 | Kirsch |
| 2010/0051529 A1 | 3/2010 | Grant et al. |
| 2010/0051552 A1 | 3/2010 | Rohde |
| 2010/0076364 A1 | 3/2010 | O'Mahony et al. |
| 2010/0078381 A1 | 4/2010 | Merchant |
| 2010/0078387 A1 | 4/2010 | Wong |
| 2010/0084330 A1 | 4/2010 | Wong |
| 2010/0087771 A1* | 4/2010 | Karakama .......... A61M 1/3455 |
| | | 604/6.11 |
| 2010/0094158 A1 | 4/2010 | Solem |
| 2010/0100027 A1 | 4/2010 | Schilthuizen |
| 2010/0101195 A1 | 4/2010 | Clements |
| 2010/0102190 A1 | 4/2010 | Zhu et al. |
| 2010/0114001 A1 | 5/2010 | O'Mahoney |
| 2010/0114012 A1 | 5/2010 | Sandford |
| 2010/0137693 A1 | 6/2010 | Porras |
| 2010/0168546 A1 | 7/2010 | Kamath |
| 2010/0168641 A1 | 7/2010 | O'Mahoney |
| 2010/0213127 A1 | 8/2010 | Castellarnau |
| 2010/0217181 A1 | 8/2010 | Roberts |
| 2010/0224492 A1 | 9/2010 | Ding |
| 2010/0234795 A1 | 9/2010 | Wallenas |
| 2010/0241045 A1 | 9/2010 | Kelly |

(56) References Cited

U.S. PATENT DOCUMENTS

| | | |
|---|---|---|
| 2010/0252490 A1 | 10/2010 | Fulkerson |
| 2010/0312172 A1 | 12/2010 | Hoffman |
| 2010/0312174 A1 | 12/2010 | Hoffman |
| 2010/0314314 A1 | 12/2010 | Ding |
| 2010/0326911 A1 | 12/2010 | Rosenbaum |
| 2011/0009798 A1 | 1/2011 | Kelly |
| 2011/0017665 A1 | 1/2011 | Updyke |
| 2011/0048949 A1 | 3/2011 | Ding et al. |
| 2011/0066043 A1 | 3/2011 | Banet |
| 2011/0077574 A1 | 3/2011 | Sigg |
| 2011/0079558 A1 | 4/2011 | Raimann |
| 2011/0087187 A1 | 4/2011 | Beck |
| 2011/0130666 A1 | 6/2011 | Dong |
| 2011/0163034 A1 | 7/2011 | Castellarnau |
| 2011/0171713 A1 | 7/2011 | Bluchel |
| 2011/0184340 A1 | 7/2011 | Tan |
| 2011/0220562 A1 | 9/2011 | Beiriger |
| 2011/0247973 A1 | 10/2011 | Sargand |
| 2011/0272337 A1 | 11/2011 | Palmer |
| 2011/0272352 A1 | 11/2011 | Braig |
| 2011/0297593 A1 | 12/2011 | Kelly |
| 2011/0315611 A1 | 12/2011 | Fulkerson |
| 2011/0315632 A1 | 12/2011 | Freije |
| 2012/0016228 A1 | 1/2012 | Kroh |
| 2012/0018377 A1 | 1/2012 | Tsukamoto |
| 2012/0083729 A1 | 4/2012 | Childers |
| 2012/0085707 A1 | 4/2012 | Beiriger |
| 2012/0092025 A1 | 4/2012 | Volker |
| 2012/0095402 A1 | 4/2012 | Lande |
| 2012/0115248 A1 | 5/2012 | Ansyln |
| 2012/0220528 A1 | 8/2012 | VanAntwerp |
| 2012/0248017 A1 | 10/2012 | Beiriger |
| 2012/0258545 A1 | 10/2012 | Ash |
| 2012/0258546 A1 | 10/2012 | Marran |
| 2012/0273354 A1 | 11/2012 | Orhan et al. |
| 2012/0273415 A1 | 11/2012 | Gerber |
| 2012/0273420 A1 | 11/2012 | Gerber |
| 2012/0277546 A1 | 11/2012 | Soykan |
| 2012/0277551 A1 | 11/2012 | Gerber |
| 2012/0277552 A1 | 11/2012 | Gerber |
| 2012/0277604 A1 | 11/2012 | Gerber |
| 2012/0277650 A1 | 11/2012 | Gerber |
| 2012/0277655 A1 | 11/2012 | Gerber |
| 2012/0277722 A1 | 11/2012 | Gerber |
| 2012/0303079 A1 | 11/2012 | Mahajan |
| 2013/0006128 A1 | 1/2013 | Olde et al. |
| 2013/0018095 A1 | 1/2013 | Vath |
| 2013/0019179 A1 | 1/2013 | Zhao |
| 2013/0020237 A1 | 1/2013 | Wilt et al. |
| 2013/0023812 A1 | 1/2013 | Hasegawa et al. |
| 2013/0025357 A1 | 1/2013 | Noack et al. |
| 2013/0027214 A1 | 1/2013 | Eng |
| 2013/0028809 A1 | 1/2013 | Barton |
| 2013/0030347 A1 | 1/2013 | Sugioka |
| 2013/0030348 A1 | 1/2013 | Lauer |
| 2013/0030356 A1 | 1/2013 | Ding |
| 2013/0037142 A1 | 2/2013 | Farrell |
| 2013/0037465 A1 | 2/2013 | Heyes |
| 2013/0056418 A1 | 3/2013 | Kopperschmidt et al. |
| 2013/0072895 A1 | 3/2013 | Kreischer et al. |
| 2013/0075314 A1 | 3/2013 | Nikolic |
| 2013/0087210 A1 | 4/2013 | Brandl et al. |
| 2013/0110028 A1 | 5/2013 | Bachmann et al. |
| 2013/0116578 A1 | 5/2013 | An |
| 2013/0199998 A1 | 8/2013 | Kelly |
| 2013/0213890 A1 | 8/2013 | Kelly |
| 2013/0213891 A1 | 8/2013 | Karoor |
| 2013/0226065 A1 * | 8/2013 | Wolff .................... A61M 1/30 604/5.01 |
| 2013/0228516 A1 | 9/2013 | Jonsson |
| 2013/0274642 A1 | 10/2013 | Soykan |
| 2013/0324915 A1 | 12/2013 | (Krensky)Britton |
| 2013/0330208 A1 | 12/2013 | Ly |
| 2013/0331774 A1 | 12/2013 | Farrell |
| 2014/0001112 A1 | 1/2014 | Karoor |
| 2014/0018728 A1 | 1/2014 | Plahey |
| 2014/0042092 A1 | 2/2014 | Akonur |
| 2014/0065950 A1 | 3/2014 | Mendelsohn |
| 2014/0088442 A1 | 3/2014 | Soykan |
| 2014/0110340 A1 | 4/2014 | White |
| 2014/0110341 A1 | 4/2014 | White |
| 2014/0138294 A1 | 5/2014 | Fulkerson |
| 2014/0158538 A1 | 6/2014 | Collier |
| 2014/0158588 A1 | 6/2014 | Pudil |
| 2014/0158623 A1 | 6/2014 | Pudil |
| 2014/0190876 A1 | 7/2014 | Meyer |
| 2014/0190885 A1 | 7/2014 | Meyer |
| 2014/0190886 A1 | 7/2014 | Pudil |
| 2014/0190891 A1 | 7/2014 | Lura |
| 2014/0217028 A1 | 8/2014 | Pudil |
| 2014/0217030 A1 | 8/2014 | Meyer |
| 2014/0220699 A1 | 8/2014 | Pudil |
| 2014/0251908 A1 | 9/2014 | Ding |
| 2014/0326671 A1 | 11/2014 | Kelly |
| 2014/0336568 A1 | 11/2014 | Wong |
| 2015/0057602 A1 | 2/2015 | Mason |
| 2015/0108069 A1 | 4/2015 | Merchant et al. |
| 2015/0108609 A1 | 4/2015 | Kushida |
| 2015/0114891 A1 | 4/2015 | Meyer |
| 2015/0144539 A1 | 5/2015 | Pudil |
| 2015/0144542 A1 | 5/2015 | Pudil |
| 2015/0157960 A1 | 6/2015 | Pudil |
| 2015/0238673 A1 | 8/2015 | Gerber |
| 2015/0250937 A1 | 9/2015 | Pudil |
| 2015/0251161 A1 | 9/2015 | Pudil |
| 2015/0251162 A1 | 9/2015 | Pudil |
| 2015/0258266 A1 | 9/2015 | Merchant |
| 2015/0306292 A1 | 10/2015 | Pudil |
| 2015/0367051 A1 | 12/2015 | Gerber |
| 2015/0367052 A1 | 12/2015 | Gerber |
| 2015/0367055 A1 | 12/2015 | Pudil |
| 2015/0367056 A1 | 12/2015 | Gerber |
| 2015/0367057 A1 | 12/2015 | Gerber |
| 2015/0367058 A1 | 12/2015 | Gerber |
| 2015/0367059 A1 | 12/2015 | Gerber |
| 2015/0367060 A1 | 12/2015 | Gerber |
| 2016/0236188 A1 | 8/2016 | Menon |
| 2016/0243540 A1 | 8/2016 | Menon |
| 2016/0243541 A1 | 8/2016 | Menon |
| 2017/0087291 A1 * | 3/2017 | Gerber ................ A61M 1/1603 |
| 2018/0221554 A1 * | 8/2018 | Mazack ............. A61M 1/1656 |

FOREIGN PATENT DOCUMENTS

| | | |
|---|---|---|
| CN | 103402563 A | 11/2013 |
| CN | 104936633 | 9/2015 |
| CN | 105658326 A | 6/2016 |
| DE | 3110128 A1 | 9/1982 |
| DE | 102011052188 | 1/2013 |
| EP | 0266795 A2 | 11/1987 |
| EP | 0264695 | 4/1988 |
| EP | 0614081 B1 | 7/2000 |
| EP | 1085295 | 11/2001 |
| EP | 711182 B1 | 6/2003 |
| EP | 1364666 A1 | 11/2003 |
| EP | 0906768 B1 | 2/2004 |
| EP | 1701752 A2 | 9/2006 |
| EP | 1450879 | 10/2008 |
| EP | 2100553 A1 | 9/2009 |
| EP | 2575827 A2 | 12/2010 |
| EP | 2576453 A2 | 12/2011 |
| EP | 2446908 | 5/2012 |
| EP | 2701580 | 11/2012 |
| EP | 2701595 | 11/2012 |
| EP | 1545652 B1 | 1/2013 |
| EP | 1684625 B1 | 1/2013 |
| EP | 2142234 B1 | 1/2013 |
| EP | 2550984 A1 | 1/2013 |
| EP | 1345856 B1 | 3/2013 |
| EP | 1938849 B1 | 3/2013 |
| EP | 2219703 B1 | 3/2013 |
| EP | 2564884 A1 | 3/2013 |
| EP | 2564885 A1 | 3/2013 |
| EP | 2344220 B1 | 4/2013 |

(56)                References Cited

FOREIGN PATENT DOCUMENTS

| EP | 1345687 | | 6/2013 |
|----|---------|----|--------|
| EP | 2701596 | | 3/2014 |
| EP | 1991289 | B1 | 6/2015 |
| JP | S5070281 | A | 6/1975 |
| JP | S51-55193 | | 5/1976 |
| JP | S51-131393 | | 11/1976 |
| JP | S61164562 | | 7/1986 |
| JP | 2981573 | | 11/1999 |
| JP | 2005511250 | | 4/2005 |
| JP | 200744602 | | 2/2007 |
| JP | NPL604 | | 2/2007 |
| JP | 5-99464 | | 10/2012 |
| JP | 2013502987 | | 10/2013 |
| WO | 9106326 | A1 | 5/1991 |
| WO | 9532010 | A1 | 11/1995 |
| WO | 19937342 | A1 | 7/1999 |
| WO | 2000038591 | A2 | 7/2000 |
| WO | 0057935 | | 10/2000 |
| WO | 200066197 | A1 | 11/2000 |
| WO | 200170307 | A1 | 9/2001 |
| WO | 2001085295 | A2 | 9/2001 |
| WO | 0185295 | A2 | 11/2001 |
| WO | 2002043859 | | 6/2002 |
| WO | 2003043677 | A2 | 5/2003 |
| WO | 2003043680 | | 5/2003 |
| WO | WO 2003041764 | | 5/2003 |
| WO | 2003051422 | A2 | 6/2003 |
| WO | 2004008826 | | 1/2004 |
| WO | 2004009156 | | 1/2004 |
| WO | 2004030716 | A2 | 4/2004 |
| WO | 2004030717 | A2 | 4/2004 |
| WO | 2004064616 | A2 | 8/2004 |
| WO | 2004062710 | A3 | 10/2004 |
| WO | WO 2005/062973 | A3 | 7/2005 |
| WO | 2005123230 | | 12/2005 |
| WO | 2007089855 | A2 | 8/2007 |
| WO | WO 20070103411 | | 9/2007 |
| WO | 2008075951 | A1 | 6/2008 |
| WO | 2009026603 | | 12/2008 |
| WO | 2009064984 | | 5/2009 |
| WO | 2009157877 | A1 | 12/2009 |
| WO | 2009157878 | A1 | 12/2009 |
| WO | 20090157877 | | 12/2009 |
| WO | 2010102190 | A4 | 11/2010 |
| WO | 2010141949 | | 12/2010 |
| WO | WO 2011/017215 | | 2/2011 |
| WO | 2011025705 | A1 | 3/2011 |
| WO | 2012148781 | | 11/2012 |
| WO | 2012148786 | | 11/2012 |
| WO | 2012148789 | | 11/2012 |
| WO | 2012162515 | A2 | 11/2012 |
| WO | 2012172398 | | 12/2012 |
| WO | 2013019179 | A1 | 2/2013 |
| WO | 2013022024 | A1 | 2/2013 |
| WO | 2013022837 | A1 | 2/2013 |
| WO | 2013025844 | | 2/2013 |
| WO | 2013027214 | | 2/2013 |
| WO | 2013028809 | A2 | 2/2013 |
| WO | WO 2013/019179 | | 2/2013 |
| WO | WO 2013/019994 | | 2/2013 |
| WO | WO 2013-025957 | | 2/2013 |
| WO | WO 2013-028809 | | 2/2013 |
| WO | WO2014121238 | A1 | 2/2013 |
| WO | 2013030642 | A1 | 3/2013 |
| WO | 2013030643 | A1 | 3/2013 |
| WO | 2013019994 | A3 | 4/2013 |
| WO | 2012060700 | | 5/2013 |
| WO | 2013101888 | | 7/2013 |
| WO | 2013103607 | A1 | 7/2013 |
| WO | 2013103906 | | 7/2013 |
| WO | WO 2013/103607 | | 7/2013 |
| WO | WO 2013109922 | | 7/2013 |
| WO | 2013114063 | A1 | 8/2013 |
| WO | 2013121162 | A1 | 8/2013 |
| WO | 14066254 | | 5/2014 |
| WO | 14066255 | | 5/2014 |
| WO | 14077082 | | 5/2014 |
| WO | 2014121162 | | 8/2014 |
| WO | 2014121163 | | 8/2014 |
| WO | 2014121167 | | 8/2014 |
| WO | 2014121169 | | 8/2014 |
| WO | WO 2015/080895 | | 4/2015 |
| WO | WO 2015060914 | | 4/2015 |
| WO | WO 2015/126879 | | 8/2015 |
| WO | 2015142624 | | 9/2015 |
| WO | 2015199764 | | 12/2015 |
| WO | WO 2015-199863 | | 12/2015 |
| WO | WO 2015-199864 | | 12/2015 |
| WO | WO 2015199765 | | 12/2015 |
| WO | WO 2016/191039 | | 12/2016 |

OTHER PUBLICATIONS

U.S. Appl. No. 13/757,709, filed Feb. 1, 2013, Medtronic.
U.S. Appl. No. 13/757,728, filed Feb. 1, 2013, Medtronic.
U.S. Appl. No. 13/836,538, filed Mar. 15, 2013, Medtronic.
European Search Report for App. No. 18153940.4, Dated Jun. 12, 2018.
European Search Report for EP 15811439, dated Feb. 15, 2018.
European Search Report for EP App. No. 15810804.3, dated Feb. 15, 2018.
European Search Report for EP App. No. 15811326.6, dated Feb. 14, 2018.
European Search Report for EP App. No. 15811573.3, dated Feb. 15, 2018.
European Search Report for EP App. No. 15812413.1, dated Feb. 2, 2018.
European Search Report in EP 15811454, dated Feb. 15, 2018.
European Search Report in EP 15812559.1, dated Jan. 31, 2018.
Office Action in Japanese Application No. 2016-553344, dated Apr. 24, 2018.
PCT/US2016/030304_IPRP.
PCT/US2016/030319_IPRP.
Search Report for Brazilian App. No. BR112016019111, dated Mar. 12, 2020.
Search Report for EP App. No. 17203984.4, dated Mar. 29, 2018.
Search Report in EP App. No. 15752771, Dated Nov. 22, 2017.
U.S. Appl. No. 61/7160,033, filed Feb. 1, 2013, Medtronic.
[NPL105] Brynda, et. al., The detection of toman 2-microglcbuiin by grating coupler immunosensor with three dimensional antibody networks. Biosensors & Bioelectronics, 1999, 363-368, 14(4).
[NPL10] Wheaton, et al., Dowex Ion Exchange Resins-Fundamentals of Ion Exchange; Jun. 2000, pp. 1-9. http://www.dow.com/scripts/litorder.asp?filepath=liquidseps/pdfs/noreg/177-01837.pdf.
[NPL111] Zhong, et. al., Miniature urea sensor based on $H(+)$-ion sensitive field effect transistor and its application in clinical analysis, Chin. J. Biotechnol., 1992, 57-65. 8(1).
[NPL119] PCT/US2012/034331, International Search Report and Written Opinion dated Jul. 9, 2012.
[NPL121] Roberts M, The regenerative dialysis (REDY) sorbent system. Nephrology, 1998, 275-278:4.
[NPL142] Hemametrics, Crit-Line Hematocrit Accuracy, 2003, 1-5, vol. 1, Tech Note No. 11 (Rev. D).
[NPL144] Weissman, S., et al., Hydroxyurea-induced hepatitis in human immunodeficiency virus-positive patients. Clin. Infec. Dis, (Jul. 29, 1999): 223-224.
[NPL146] PCT/US2012/034334, International Search Report, Jul. 6, 2012.
[NPL147] PCT/US2012/034335, International Search Report, Sep. 5, 2012.
[NPL148] PCT/US/2012/034327, International Search Report, Aug. 13, 2013.
[NPL149] PCT/US/2012/034329, International Search Report, Dec. 3, 2012.
[NPL162] International Search Report from PCT/US2012/051946 mailed Mar. 4, 2013.

(56)     References Cited

OTHER PUBLICATIONS

[NPL169] Wang, Fundamentals of intrathoracic impedance monitoring in heart failure, Am. J. Cardiology, 2007, 3G-10G: Suppl.
[NPL16] PCT/US2014/067650 International Search Report Written Opinion mailed Mar. 9, 2015.
[NPL176] Bleyer, et. al., Sudden and cardiac death rated in hemodialysis patients, Kidney International. 1999, 1553-1559: 55.
[NPL187] PCT/US2012/034333, International Preliminary Report on Patentability, Oct. 29, 2013.
[NPL188] PCT/US2012/034333, International Search Report, Aug. 29, 2012.
[NPL197] PCT/US2012/034330, International Preliminary Report on Patentability, Oct. 29, 2013.
[NPL1] PCT/US2014/065950 International Search Report and Written Opinion mailed Feb. 24, 2015.
[NPL205] Culleton, BF et al. Effect of Frequent Nocturnal Hemodialysis vs. Conventional Hemodialysis on Left Ventricular Mass and Quality of Life. 2007 Journal of the American Medical Association 298 (11), 1291-1299.
[NPL230] Redfield, et. al., Restoration of renal response to atria! natriuretic factor in experimental low-output heat failure, Am. J. Physiol., Oct. 1, 1989, R917-923:257.
[NPL231] Rogoza, et. al., Validation of A&D UA-767 device for the self-measurement of blood pressure, Blood Pressure Monitoring, 2000, 227-231, 5(4).
[NPL234] Lima, et. al., An electrochemical sensor based on nanostructure hollandite-type manganese oxide for detection of potassium ion, Sensors, Aug. 24, 2009, 6613-8625, 9.
[NPL235] Maclean, et, al., Effects of hindlimb contraction on pressor and muscle interstitial metabolite responses in the cat, J. App. Physiol., 1998, 1583-1592, 85(4).
[NPL246] PCT/US2014/014346 International Search Report and Written Opinion.
[NPL248] PCT/US2014/014345 International Search Report and Written Opinion, mailed May 2014.
[NPL264] PCT/US2014/014357 International Search Report and Written Opinion dated May 19, 2014.
[NPL268] Ronco et al. 2008, Cardiorenal Syndrome, Journal American College Cardiology, 52:1527-1539, Abstract.
[NPL26] Overgaard, et. al., Activity-induced recovery of excitability in K+-depressed rat soleus muscle, Am. J. P 280: R48-R55, Jan. 1, 2001.
[NPL27] Overgaard et. al., Relations between excitability and contractility in rate soleusmuscle: role of the NA+-K+ pump and NA+-K-S gradients. Journal of Physiology, 1999, 215-225, 518(1).
[NPL2] PCT/US2015/032492 International Search Report mailed Nov. 19, 2015.
[NPL306] Coast, et al. 1990, An approach to Cardiac Arrhythmia analysis Using Hidden Markov Models, IEEE Transactions On Biomedical Engineering. 1990, 37(9):826-835.
[NPL32] Secemsky, et. al., High prevalence of cardiac autonomic dysfunction and T-wave alternans in dialysis patients. Heart Rhythm, Apr. 2011, 592-598 : vol. 8, No. 4.
[NPL35] Wei, et. al., Fullerene-cryptand coated piezoelectric crystal urea sensor based on urease, Analytica Chimica Acta, 2001,77-85:437.
[NPL376] Gambro AK 96 Dialysis Machine Operators Manual, Dec. 2012. p. 1-140.
[NPL376] Gambro AK 96 Dialysis Machine Operators Manual, Dec. 2012. p. 141-280.
[NPL376] Gambro AK 96 Dialysis Machine Operators Manual, Dec. 2012. p. 281-420.
[NPL376] Gambro AK 96 Dialysis Machine Operators Manual, Dec. 2012. p. 421-534.
[NPL383] Leifer et al., A Study on the Temperature Variation of Rise Velocity for Large Clean Bubbles, J. Atmospheric & Oceanic Tech., vol. 17, pp. 1392-1402, Oct. 2000.
[NPL384] Talaia, Terminal Velocity of a Bubble Rise in a Liquid col. World Acad. of Sci., Engineering & Tech., vol. 28, pp. 264-268, Published Jan. 1, 2007.

[NPL386] The FHN Trial Group. In-Center. Hemodialysis Six Times per Week versus Three Times per Week, New England Journal of Medicine, 2010 Abstract.
[NPL387] Gotch FA, Sargent JA A mechanistic analysis of the National Cooperative Dialysis Study (NCDS). Kidney int. 1985: 28:526-34.
[NPL388] Daugirdas JT. Second generation logarithmic estimates of single-pool variable vol. Kt/V and analysis of error. J Am Soc Nephrol, 1993: 4:1205-13.
[NPL389] Steil et al. Intl Journ Artif Organs, 1993, In Vivo Verification of an Automatic Noninvasive System for Real Time Kt Evaluation, ASAIO J., 1993, 39:M348-52.
[NPL39] PCT/US2012/034332, International Search Report, Jul. 5, 2012.
[NPL3] PCT/US2015/019901 International Search Report and Written Opinion mailed Jun. 5, 2015.
[NPL46] Siegenthaler, et al., Pulmonary fluid status monitoring with intrathoracic impedance, Journal of Clinical Monitoring and Computing, 24:449-451, published Jan. 12, 2011.
[NPL494] John Wm Agar: Review: Understanding sorbent dialysis systems, Nephrology, vol. 15, No. 4, Jun. 1, 2010, pp. 406-411.
[NPL499] Ep. App. 14746193.3 Search Report dated Oct. 19, 2016.
[NPL4] PCT/US2015/016270 International Search Report and Written Opinion mailed Jun. 5, 2015.
[NPL518] Office Action in U.S. Appl. No. 14/269,589, Dated Nov. 4, 2016.
[NPL532] Eureopean Search Report for App. No. EP14745643 Dated Oct. 6, 2016.
[NPL534] Office Action in U.S. Appl. No. 13/586,824 Dated Dec. 21, 2015.
[NPL548] PCT/US15/18587 International Preliminary Report on Patentability Dated Jun. 6, 2016.
[NPL550] European Search Opinion for App. No. EP12826180 Dated Mar. 19, 2015.
[NPL551] European Search Opinion for App. No. EP12826180 Dated Jan. 18, 2016.
[NPL552] Khanna, Ramesh, R.T. Krediet, and Karl D. Nolph. Nolph and Gokals Textbook of Peritoneal Dialysis New York: Springer 2009. Print.
[NPL553] Ruperez et al., Comparison of a tubular pulsatile pump and a volumetric pump for continuous venovenous renal replacement therapy in a pediatric animal model, 51 ASAIO J. 372, 372-375 (2005).
[NPL554] St. Peter et al., Liver and kidney preservation by perfusion, 359 The Lancet 604, 606(2002).
[NPL555] Dasselaar et al., Measurement of relative blood volume changes during hemodialysis: merits and limitations, 20 Nephrol Dial Transpl. 2043, 2043-2044 (2005).
[NPL556] Ralph T. Yang, Adsorbents: Fundamentals and Applications 109 (2003).
[NPL557] Henny H. Billett, Hemoglobin and Hematocrit, in Clinical Methods: The History, Physical, and Laboratory Examinations 719(HK Walker, WD Hall, & JW Hurst ed., 1990).
[NPL558] Office Action in U.S. Appl. No. 13/565,733 Dated Jan. 11, 2016.
[NPL559] Office Action in U.S. Appl. No. 13/565,733 Dated Jun. 11, 2015.
[NPL560] Office Action in U.S. Appl. No. 13/586,824 Dated Jun. 4, 2015.
[NPL561] Office Action in U.S. Appl. No. 13/757,792 Dated Jun. 2, 2016.
[NPL562] Office Action in U.S. Appl. No. 13/757,796 Dated Apr. 13, 2015.
[NPL563] Office Action in U.S. Appl. No. 13/757,796 Dated Dec. 21, 2015.
[NPL564] Office Action in U.S. Appl. No. 13/835,735 Dated Oct. 13, 2015.
[NPL565] Office Action in U.S. Appl. No. 13/836,079 Dated Apr. 17, 2015.
[NPL566] Office Action in U.S. Appl. No. 13/836,079 Dated Jun. 30, 2016.
[NPL569] Office Action in U.S. Appl. No. 13/791,755 Dated Mar. 16, 2016.

(56)  References Cited

OTHER PUBLICATIONS

[NPL570] Office Action in U.S. Appl. No. 13/791,755 Dated Aug. 9, 2016.

[NPL571] Office Action in U.S. Appl. No. 13/835,735 Dated Jun. 16, 2016.

[NPL572] Office Action in U.S. Appl. No. 13/836,079 Dated Nov. 6, 2015.

[NPL584] Office Action in App. No. AU 2015280604 mailed Apr. 8, 2016.

[NPL586] International Search Report from International Application No. PCT/US2014/014347 dated May 9, 2014.

[NPL590] PCT/US2016/030319 Written Opinion mailed Jul. 27, 2016.

[NPL591] PCT/US2016/030320 Written Opinion mailed Jul. 27, 2016.

[NPL596] PCT/US2012/014347, International Search Report.

[NPL5] PCT/US2015/016273 International Search Report and Written Opinion mailed Jun. 9, 2015.

[NPL601] Wester et al., A regenerable postassium and phosphate sorbent system to enhance dialysis efficacy and device portability: an in vitro study Nephrol Dial Transplant (2013) 28: 2364-2371 Jul. 3, 2013.

[NPL602] Office Action in App. No. JP 2016-515476 mailed Dec. 26, 2016.

[NPL603] Japanese Patent Publication No. S50-70281A.

[NPL605] PCT/US2015/032494 Written Opinion mailed Nov. 19, 2015.

[NPL606] PCT/US2015/032494 International Search Report mailed Nov. 19, 2015.

[NPL607] PCT/US2015/019901 International Preliminary Report on Patentability mailed May 27, 2016.

[NPL608] PCT/US2015/019901 Written Opinion mailed May 27, 2016.

[NPL609] PCT/US2015/019901 Written Opinion mailed Jun. 5, 2015.

[NPL610] PCT/US2015/019901 International Search Report mailed Jun. 5, 2015.

[NPL611] PCT/US2015/032485 International Preliminary Report on Patentability mailed May 11, 2016.

[NPL612] PCT/US2015/032485 International Preliminary Report on Patentability mailed May 11, 2016.

[NPL613] PCT/US20115/032485 International Preliminary Report on Patentability mailed May 11, 2016.

[NPL614] PCT/US2016/030304 International Search Report mailed Jul. 27, 2016.

[NPL615] PCT/US2016/030304 Written Opinion mailed Jul. 27, 2016.

[NPL616] PCT/US2016/030312 Written Opinion mailed Jul. 28, 2016.

[NPL617] PCT/US2016/030312 International Search Report mailed Jul. 28, 2016.

[NPL618] PCT/US2016/030319 International Search Report mailed Jul. 27, 2016.

[NPL619] PCT/US2016/030319 Written Opinion mailed Jul. 27, 2016.

[NPL620] PCT/US2016/030320 Written Opinion mailed Jul. 28, 2016.

[NPL621] PCT/US2016/030320 International Search Report mailed Jul. 28, 2016.

[NPL622] PCT/US2015/032485 Written Opinion mailed Oct. 16, 2015.

[NPL623] PCT/US2015/032485 Written Opinion mailed Oct. 16, 2016.

[NPL626] PCT/US2015/032485 International Search Report and Written Opinion mailed Oct. 16, 2015.

[NPL62] U.S. Appl. No. 13/424,533, dated Nov. 1, 2012.

[NPL634] PCT/US2016/030320 International Preliminary Report on Patentability, mailed Apr. 20, 2017.

[NPL654] International Preliminary Report from International Application No. PCT/US2014/014348 dated Jan. 9, 2015.

[NPL655] European Search Report from European Application No. EP 14746193.3 dated Oct. 19, 2016.

[NPL656] European Search Report from European Application No. EP 14746193.3 dated Jun. 8, 2016.

[NPL657] PCT/US2014/014345 Written Opinion dated Jun. 24, 2015.

[NPL658] PCT/US2014/014345 International Search Report and Written Opinion dated May 30, 2014.

[NPL659] Office Action in European Application No. 14746428.03 dated Feb. 8, 2017.

[NPL660] European Search Report in European Application No. 14746428.03 dated Aug. 25, 2016.

[NPL661] PCT/US2014/014346 Writtent Opinion dated Apr. 10, 2015.

[NPL662] PCT/US2014/014346 International Search Report and Writtent Opinion dated May 23, 2014.

[NPL663] EP 14746415.0 European Search Report dated Aug. 22, 2016.

[NPL664] Office Action in European Application No. EP 14746415.0 dated Apr. 19, 2017.

[NPL670] Office Action in European Application No. 14746415.0 dated Apr. 19, 2017.

[NPL681] PCT/US2015/020047 International Search Report and Written Opinion mailed Jun. 29, 2015.

[NPL682] PCT/US2015/020047 International Preliminary Report on Patentability mailed Jun. 30, 2015.

[NPL684] PCT/US2015/020044 Written Opinion dated Jun. 21, 2016.

[NPL685] PCT/US2015/020044 International Preliminary Report on Patentability dated Nov. 4, 2016.

[NPL686] PCT/US2015/020044 International Search Report dated Jun. 30, 2015.

[NPL688] US2015/019881 Written Opinion dated Jun. 16, 2016.

[NPL689] US2015/019881 Written Opinion dated May 9, 2016.

[NPL690] US2015/019881 International Search Report and Written Opinion dated Jun. 29, 2015.

[NPL692] PCT/US2014/065950 International Preliminary Report on Patentability mailed Oct. 28, 2015.

[NPL696] PCT/US2015/032485 Written Opinion mailed May 9, 2016.

[NPL6] PCT/US2015/032492 Written Opinion mailed Nov. 19, 2015.

[NPL720] PCT/US2015/019901 International Search Report and Written Opinion mailed Jun. 5, 2015.

[NPL721] PCT/US2015/019901 International Preliminary Report on Patentability mailed May 27, 2016.

[NPL722] PCT/US2015/032494 International Preliminary Report on Patentablity mailed Dec. 27, 2016.

[NPL730] Office Action for Chinese Application No. 201580009562.5 dated Jul. 3, 2017.

[NPL734] International Preliminary Report on Patentability for Application No. PCT/US2015/032492 dated Jun. 30, 2017.

[NPL736] Office Action in European Application No. 14746193.3 dated Apr. 19, 2017.

[NPL737] International Preliminary Report on Patentability for Application No. PCT/US2015/016273 dated Feb. 19, 2016.

[NPL747] European Search Report for App. No. 15751391.2 dated Aug. 4, 2017.

[NPL755] European Search Report and supplementary Search Report for App. No. 14865374.4 dated Jun. 12, 2017.

[NPL756] European Search Report and Supplemental Search Report in European Application No. 14865374.4 dated Jun. 12, 2017.

[NPL7] PCT/US2015/020046 International Search Report and Written Opinion mailed Jun. 29, 2015.

[NPL8] PCT/US2015/020044 International Search Report Written Opinion mailed Jun. 30, 2015.

[NPL90] Nedelkov, et. al., Design of buffer exchange surfaces and sensor chips for biosensor chip mass spectrometry, Proteomics, 2002, 441-446, 2(4).

[NPL] European Search Report App 14865374.4, Jun. 12, 2017.

Chinese Office Action for App. No. 201580034005.9, dated Dec. 12, 2018.

(56)         References Cited

OTHER PUBLICATIONS

Chinese Office Action in App. No. 201580009563.X, dated Mar. 13, 2018.
European Search Report for App. No. 15812081.6, dated Mar. 8, 2018.

* cited by examiner

INCREASED OPERATIONAL CAPABILITIES OF A DIALYSIS SYSTEM

FIELD

The disclosure relates to systems and methods for increasing the functional capabilities of a sorbent-based dialysis system. The systems and methods allow for the mode of operation of the dialysis system to be switched between single pass mode and a sorbent based multi-pass mode by controlling an amount of water added to the dialysate between 0% to 100% of the dialysate flow rate.

BACKGROUND

Sorbent-based multi-pass dialysis systems can reduce the volume of purified water needed for therapy. Sorbent cartridges operate by adsorbing ions and other waste solutes from spent dialysate, allowing the repurified water to be reused. Often urea in the dialysate is catalytically converted to ammonium ions, which are removed by zirconium phosphate or other cation exchange resin in the sorbent cartridge. However, large or highly uremic patients may result in the capacity of zirconium phosphate to adsorb solutes from the dialysate to be exceeded. After the sorbent cartridge capacity is exceeded, therapy must be halted to prevent ammonia or ammonium ions from being passed into the blood of the patient across the dialyzer. Further, sulfate and nitrate are ions may be difficult to remove using sorbent dialysis due to low capacity of the sorbent material for these anions.

Hence, there is a need for systems and methods that can increase the functional capabilities of a sorbent-based dialysis system, allowing full treatment even of large or more uremic patients. There is a need for systems and methods that can provide treatment to these patients with standard size and capacity sorbent cartridges. The need extends for systems and methods that blend single pass and multi-pass dialysis to provide the necessary treatment to patients while still using a reduced volume of water compared to traditional single pass systems.

SUMMARY OF THE INVENTION

The problem to be solved by the present invention is to increase the functional capabilities of a multi-pass dialysis system to allow therapy for larger or more uremic patients without stopping therapy due to exceeding the capacity of a sorbent cartridge. The solution is to control a mode of operation of the dialysis system by controlling a water addition rate to prevent the sorbent cartridge capacity from being exceeded.

The first aspect of the invention relates to a system. In any embodiment, the system can include a fluid flow path, having i) a dialyzer outlet fluidly connectable to a dialyzer; ii) a first valve fluidly connecting the fluid flow path to a drain line; iii) a sorbent cartridge positioned downstream of the first valve; iv) a second valve fluidly connecting the fluid flow path to a water source; the second valve upstream of the sorbent cartridge; and v) a dialyzer inlet downstream of the sorbent cartridge; the system including an infusate source fluidly connectable to the fluid flow path downstream of the second valve and upstream of the dialyzer inlet; and a control system; the control system programmed to control a mode of operating the fluid flow path between a first mode of operation and a second mode of operation by controlling the first valve and the second valve; wherein the control system can be programmed to switch the mode of operation during a dialysis session.

In any embodiment, the first mode of operation can be a single pass mode and the second mode of operation can be a multi-pass mode.

In any embodiment, the first mode of operation can be a multi-pass mode and the second mode of operation can be a single pass mode.

In any embodiment, the first mode of operation be a first water addition rate and the second mode of operation be a second water addition rate.

In any embodiment, the control system can be programmed to switch from the first mode of operation to second mode of operation at a predetermined time during the dialysis session.

In any embodiment, the control system can be programmed to determine the predetermined time based on one or more patient parameters.

In any embodiment, the control system can be programmed to determine the predetermined time based on a sorbent cartridge capacity.

In any embodiment, the predetermined time can be based on a patient weight.

In any embodiment, the predetermined time can be based on at least one of a patient BUN level, a bicarbonate prescription, blood flow rate, dialysate flow rate, dialyzer koA, and patient volume.

In any embodiment, the predetermined time can be based on a patient bicarbonate level.

In any embodiment, the predetermined time can be based on a dialysate bicarbonate level.

In any embodiment, the system can include at least one sensor between the dialyzer outlet and the first valve.

In any embodiment, the control system can be programmed to determine a percent clearance for a dialysis session based on the at least one sensor.

In any embodiment, the control system can be programmed to switch the mode of operation at a predetermined percent clearance.

In any embodiment, the sensor can measure either creatinine or urea.

In any embodiment, the control system can be programmed to determine if a sorbent cartridge capacity has been reached based on at least one sensor downstream of the sorbent cartridge.

In any embodiment, the control system can be programmed to switch from a multi-pass mode to a single pass mode if the sorbent cartridge capacity has been reached.

The features disclosed as being part of the first aspect of the invention can be in the first aspect of the invention, either alone or in combination, or follow any arrangement or permutation of any one or more of the described elements. Similarly, any features disclosed as being part of the first aspect of the invention can be in a second aspect of the invention described below, either alone or in combination, or follow any arrangement or permutation of any one or more of the described elements.

The second aspect of the invention relates to a method. In any embodiment, the method can include the steps of initiating a dialysis session with a first mode of operation by controlling a water addition rate.

In any embodiment, the first mode of operation can be a single pass mode and the second mode of operation can be a multi-pass mode of operation.

In any embodiment, the first mode of operation can be a multi-pass mode and the second mode of operation can be a single pass mode of operation.

In any embodiment, the first mode of operation can be a first water addition rate and the second mode of operation can be a second water addition rate.

In any embodiment, the step of switching from the first mode of operation to the second mode of operation can be at a predetermined time.

In any embodiment, a predetermined time for switching from the first mode of operation to the second mode of operation can be based on one or more patient parameters.

In any embodiment, the method can use a sorbent cartridge, and a predetermined time for switching from the first mode of operation to the second mode of operation can be based on a capacity of the sorbent cartridge.

In any embodiment, a predetermined time for switching from the first mode of operation to the second mode of operation can be based on patient weight.

In any embodiment, a predetermined time for switching from the first mode of operation to the second mode of operation can be based on at least one of a patient BUN level, a bicarbonate prescription, blood flow rate, dialysate flow rate, dialyzer koA, patient bicarbonate level, and patient volume.

In any embodiment, the method can be performed by the control system of the system of the first aspect of the invention.

In any embodiment, the method can include a step of monitoring a percent clearance during the dialysis session.

In any embodiment, the step of switching from the first mode of operation to the second mode of operation can be at a predetermined percent clearance.

In any embodiment, the percent clearance can be determined based on one or more sensors in a fluid flow path of a dialysis system.

The features disclosed as being part of the second aspect of the invention can be in the second aspect of the invention, either alone or in combination, or follow any arrangement or permutation of any one or more of the described elements. Similarly, any features disclosed as being part of the second aspect of the invention can be in the first aspect of the invention, either alone or in combination, or follow any arrangement or permutation of any one or more of the described elements.

DETAILED DESCRIPTION

Figure 1:
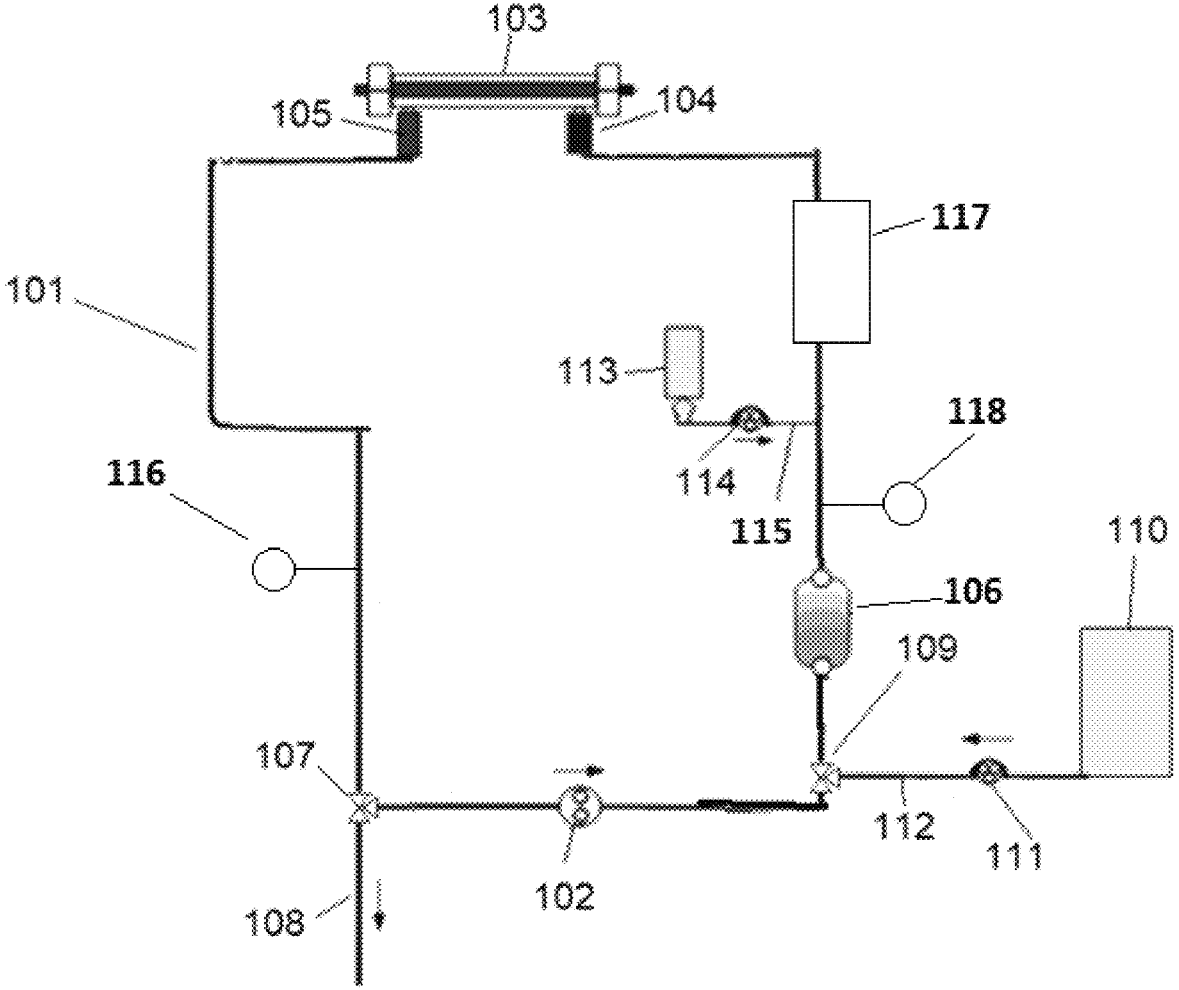
FIG. 1 illustrates a system for improving the operation capabilities of a dialysis system.

Unless defined otherwise, all technical and scientific terms used have the same meaning as commonly understood by one of ordinary skill in the art.

The articles "a" and "an" are used to refer to one to over one (i.e., to at least one) of the grammatical object of the article. For example, "an element" means one element or over one element.

The term "bicarbonate prescription" refers to a bicarbonate concentration of a dialysate to be used in a dialysis session.

The term "blood flow rate" refers to a rate of blood entering or exiting a dialyzer.

The term "comprising" includes, but is not limited to, whatever follows the word "comprising." Use of the term indicates the listed elements are required or mandatory but that other elements are optional and may be present.

The term "consisting of" includes and is limited to whatever follows the phrase "consisting of." The phrase indicates the limited elements are required or mandatory and that no other elements may be present.

The term "consisting essentially of" includes whatever follows the term "consisting essentially of" and additional elements, structures, acts or features that do not affect the basic operation of the apparatus, structure or method described.

The terms "control," "controlling," or "controls" refer to the ability of one component to direct the actions of one or more second or other components.

A "control system" can be a device that monitors and affects the operational conditions of a given system. The operational conditions are typically referred to as output variables of the system wherein the output variables can be affected by adjusting certain input variables. The control system can be any number or combination of processors, controllers, software, and computers.

The term "creatinine" refers to a compound having a formula $C_4H_7N_3O$ released by muscle and protein metabolism.

The terms "determining," "determines," and the like, generally refer to, in the broadest reasonable interpretation, any process or method for obtaining or coming to a decision, value, number, or finding, for any one or more value, output, parameter, or variable, by any means applicable to the relevant parameter being determined.

The term "dialysate flow rate" refers to a rate of dialysate entering or exiting a dialyzer.

A "dialysis session" can be any time period of any length during which a patient is treated by or undergoes dialysis, hemodialysis, hemofiltration, ultrafiltration, or other fluid removal therapy.

The term "dialyzer" refers to a cartridge or container with two flow paths separated by semi-permeable membranes. One flow path is for blood and one flow path is for dialysate. The membranes can be in hollow fibers, flat sheets, or spiral wound or other conventional forms known to those of skill in the art. Membranes can be selected from the following materials of polysulfone, polyethersulfone, poly (methyl methacrylate), modified cellulose, or other materials known to those skilled in the art.

The term "dialyzer koA" refers to the dialyzer mass transfer-area coefficient, which is a measure of dialyzer efficiency in clearing urea and other solutes.

The term "downstream" refers to a position of a first component in a flow path relative to a second component wherein fluid will pass by the first component after the second component during normal operation. The first component can be said to be "downstream" of the second component, while the second component is "upstream" of the first component.

A "drain line" is a fluid line leading to a drain or a waste container to remove waste fluid.

A "fluid flow path" refers to a pathway through which a fluid can travel.

The term "fluidly connectable" refers to the ability to provide passage of fluid, gas, or combinations thereof, from one point to another point. The ability to provide such passage can be any mechanical connection, fastening, or forming between two points to permit the flow of fluid, gas, or combinations thereof. The two points can be within or between any one or more of compartments, modules, systems, components, and rechargers, all of any type. Notably, the components that are fluidly connectable, need not be a part of a structure. For example, an outlet "fluidly connectable" to a pump does not require the pump, but merely that the outlet has the features necessary for fluid connection to the pump.

The term "fluidly connected" refers to a particular state or configuration of one or more components such that fluid, gas, or combination thereof, can flow from one point to another point. The connection state can also include an optional unconnected state or configuration, such that the two points are disconnected from each other to discontinue flow. It will be further understood that the two "fluidly connectable" points, as defined above, can form a "fluidly connected" state. The two points can be within or between any one or more of compartments, modules, systems, components, all of any type.

The terms "initiating" or to "initiate" a process refer to beginning a series of steps or operations.

An "infusate source" refers to any container or source from which a solution of one or more salts for the adjustment of the composition of a dialysate, such as salts of sodium, calcium, magnesium, potassium, and glucose can be obtained.

An "inlet" is a portion of a component through which gas, fluid, and combinations thereof can enter or exit the component. Although the term inlet generally refers to an opening for entry of gas, fluid, and combinations thereof, the inlet can sometimes provide a means for exiting or exhausting the gas, fluid, and combinations thereof. For example, during a priming, cleaning, or disinfection, the inlet can be used to remove gas, fluid, and combinations thereof through the inlet. Also, during operation, the inlet can remove gas, fluid, and combinations thereof.

The term "mode of operation" refers to the way a system or component operates. For example, a dialysis system can operate as a single pass system or a multi-pass system.

The term "monitoring" or to "monitor" refers to ascertaining a state of a system or process.

The term "multi-pass mode" refers to a mode of operating a dialysis system wherein at least a portion of spent dialysate is regenerated and pumped through a dialyzer multiple times during therapy.

An "outlet" is a portion of a component through which gas, fluid, and combinations thereof can enter or exit the component. Although the term outlet generally refers to an opening for egress or exhausting of gas, fluid, and combinations thereof, the outlet can sometimes provide a means for entry of a gas, fluid, and combinations thereof. For example, during a priming, cleaning, or disinfection, the outlet can be used to backflush fluid through the outlet. Also, during operation, the outlet can also provide for re-entry of gas, fluid, and combinations thereof.

A "patient" or "subject" can be a member of any animal species, preferably a mammalian species, optionally a human. The subject can be an apparently healthy individual, an individual suffering from a disease, or an individual being treated for a disease. In certain embodiments, the patient can be a human, sheep, goat, dog, cat, mouse, or any other animal.

"Patient BUN level" can refer to the patient pre-dialysis blood urea nitrogen level, or the amount of urea within the body of a patient prior to a dialysis session. The BUN measurement is generally given in units of mg/dl.

A "patient parameter" is any data that gives relevant information about the health status and therapy requirements of a patient.

The term "patient volume" refers to the amount of water in a patient.

"Patient weight" refers to the mass of a patient using a system or component.

The term "percent clearance" refers to a fraction of the total clearance of one or more solutes expected for a dialysis session that has actually been achieved at a specified time.

A "predetermined percent clearance" is a point in a process at which a fraction of the total clearance expected, determined before the process, has been achieved.

A "predetermined time" is a point in a process, determined before the process, at which some action is taken.

The term "programmed," when referring to a processor or control system, can mean a series of instructions that cause a processor or control system to perform certain steps.

A "sensor" is a component capable of determining one or more states of one or more variables in a system.

The term "single pass mode" refers to a mode of operating a dialysis system where spent dialysate is not regenerated and is instead disposed of.

The terms "sorbent cartridge" and "sorbent container" can refer to a cartridge containing one or more sorbent materials for removing specific solutes from solution, such as urea. The term "sorbent cartridge" does not require the contents in the cartridge be sorbent based, and the contents of the sorbent cartridge can be any contents that can remove waste products from a dialysate. The sorbent cartridge may include any suitable amount of one or more sorbent materials. In certain instances, the term "sorbent cartridge" can refer to a cartridge which includes one or more sorbent materials in addition to one or more other materials capable of removing waste products from dialysate. "Sorbent cartridge" can include configurations where at least some materials in the cartridge do not act by mechanisms of adsorption or absorption. In any embodiment, a system may include a number of separate cartridges which can be physically separated or interconnected wherein such cartridges can be optionally detached and reattached as desired.

The term "sorbent cartridge capacity" refers to the amount of substances that a sorbent cartridge can adsorb or otherwise remove from a fluid before the sorbent cartridge loses substantial efficiency in removing the substance or when the sorbent cartridge buffering capability is reached.

The term "switch" refers to changing a mode of operating of a system or component.

A "system parameter" is any data that gives relevant information about a system, including concentrations of fluids to be used by the system or data concerning one or more components of the system.

The term "upstream" refers to a position of a first component in a flow path relative to a second component wherein fluid will pass by the first component before the second component during normal operation. The first component can be said to be "upstream" of the second component, while the second component is "downstream" of the first component.

The term "urea" refers to $CO(NH_2)_2$, in any form or in solution.

A "valve" is a device capable of directing the flow of fluid, gas, or a combination thereof, by opening, closing or obstructing one or more pathways to flow the fluid, gas, or combination thereof to travel in a particular path.

The term "water addition rate" refers to a rate at which water is added to a dialysis flow path.

The term "water source" refers to any source from which potable or non-potable water can be obtained.

FIG. 1 illustrates a system for improving the operational capabilities of a sorbent-based dialysis system. The dialysis system can include a fluid flow path 101 fluidly connectable to a dialyzer inlet 104 and a dialyzer outlet 105 of a dialyzer 103. Dialysate is pumped through a first side of the dialyzer 103, while blood from a patient is pumped through the opposite side. Solutes, toxins, and water can cross a dialyzer membrane (not shown) to pass from the blood into the dialysate. Pump 102 provides the driving force for moving dialysate through the fluid flow path 101.

In a sorbent based multi-pass dialysis system, spent dialysate is pumped through a sorbent cartridge 106. The sorbent cartridge 106 can contain sorbent materials, such as activated carbon, alumina and urease, zirconium phosphate, and zirconium oxide. These sorbent materials can remove waste solutes from the spent dialysate. The activated carbon in the sorbent cartridge 106 can remove non-ionic waste solutes, such as creatinine, glucose, uric acid, β2-microglobulin and other non-ionic toxins, except urea. Alternative sorbents can also be used that can remove urea directly. The urease can catalyze the breakdown of urea into ammonia and carbon dioxide, resulting in ammonium carbonate. Excess carbon dioxide can be removed from the system by degasser 117. The alumina can serve as a support for the urease catalyst and adsorb some uremic toxins and water impurities. The zirconium phosphate can remove the generated ammonium cations, as well as potassium, magnesium, calcium, and other cations in the dialysate, replacing these ions with sodium or hydrogen ions originally bound to the zirconium phosphate. The zirconium oxide can remove fluoride, phosphate, and other anions from the dialysate, replacing these ions with hydroxide or acetate anions originally bound to the zirconium oxide. In certain embodiments, other cation and anion exchange materials can be used in place of the zirconium phosphate and zirconium oxide. One of skill in the art will understand that the sorbent cartridge 106 need not contain every sorbent material listed, and can include less or more sorbent materials depending on the needs of the system. One of skill in the art will also understand that the sorbent materials can be placed in the sorbent cartridge 106 in any order, or can be intermixed within the sorbent cartridge 106, so long as the cation exchange material is located downstream of the urease.

Because the cation exchange material, such as zirconium phosphate, removes potassium, calcium and magnesium from the dialysate, these ions need to be added back into the dialysate before the dialysate can be used in dialysis. Adding ions or other solutes back into the dialysate can be accomplished by use of an infusate system. Infusate source 113 can contain concentrates or solids of each of the necessary cations, as well acid, sodium chloride and sodium bicarbonate. The necessary cations can be added to the regenerated dialysate from infusate source 113 through infusate line 115 by pump 114. One of skill in the art will understand that the infusates can be located in separate containers (not shown) each with dedicated pumps and need not be present in a single container as illustrated in FIG. 1. Further, other additives may be added to the regenerated dialysate in the same fashion, such as bicarbonate or acetate buffers.

As described, the zirconium phosphate or other cation exchange resin in the sorbent cartridge 106 can remove ammonium ions generated by catalytic breakdown of urea by the urease. The zirconium phosphate also acts as a buffer depending on pH of the zirconium phosphate and removes bicarbonate as needed to maintain a certain pH. For example, zirconium phosphate with pH of 4.0 will remove sodium ions and replace the sodium ions with hydrogen ions as needed to maintain the sorbent effluent pH at 4.0. Like all buffers, the zirconium phosphate has a certain buffer capacity that can be exceeded if presented with too much base, such as bicarbonate. As such, the zirconium phosphate buffer capacity can be exceeded, similar to the adsorptive capacity. Once the capacity of the zirconium phosphate has been reached, the generated ammonium ions will pass through the sorbent cartridge into the dialysate, forcing dialysis treatment to stop. Further, even before reaching capacity, the zirconium phosphate can pH titrate due to adsorption of ammonium and other cations and reaction with bicarbonate in the spent dialysate, causing release of sulfate ions adsorbed earlier in a dialysis session. An increasing pH can also increase the bicarbonate present in the sorbent cartridge effluent, which may contribute to errors in bicarbonate control. Additionally, sulfate and nitrate ions may be difficult to remove using a sorbent cartridge due to low capacity of the sorbent material.

To avoid exceeding the capacity of the sorbent cartridge 106, delaying onset of zirconium phosphate titration, and improve removal of sulfate and nitrate ions, the system can include multiple modes of operation. A processor of a control system (not shown) can control components of the dialysis system to control the mode of operation by adjusting a water addition rate from water source 110. In certain embodiments, the control system can switch between a single pass mode and a multi-pass mode. In a single pass mode of operation, spent dialysate is not regenerated by a sorbent cartridge and is instead discarded. In the multi-pass mode of operation, at least a portion of the spent dialysate is regenerated and reused.

Valve 107 can control the movement of spent dialysate through the fluid flow path 101. When valve 107 is open to drain line 108, the spent dialysate is directed to the drain. When valve 107 is closed to drain line 108 the spent dialysate is directed through sorbent cartridge 106. To increase the operational capabilities of the system, the dialysis system can be operated in a single-pass mode for a portion of treatment and in a multi-pass mode for a portion of treatment.

In certain embodiments, valve 107 can be a proportioning valve. Valve 107 can be capable of diverting between 0%-100% of the flow to drain 108. Valve 107 can enable diversion of fraction between 0-100% to enable over dilution when the system is using multi-pass mode. In certain embodiments, the mode of operation of the dialysis system can be between single pass and multi-pass mode. Valve 107 can be operated to divert a percentage of the dialysate to the drain, and additional water can be added. For example, 50% of the dialysate can be diverted to the drain, with a volume of water added to offset the volume of dialysate removed, rather than removing only 0 or 100% of the dialysate. Removing only a portion of the dialysate reduces the amount of dialysate that passes through the sorbent cartridge, increasing the length of time before capacity is reached, while using less water than purely single-pass mode.

In the single pass mode, the spent dialysate is discarded through drain line 108, which can be fluidly connected to a drain or a waste container (not shown). Fresh water from water source 110 can be pumped into fluid flow path 101 through water line 112. Pump 111 can provide the driving force for moving water through water line 112. In single pass mode, valve 109 can be opened to the water line 112 to allow water into fluid flow path 101.

Water source 110 can contain potable water, purified water, or pre-made dialysate. If potable water is used, the water source 110 can be upstream of the sorbent cartridge 106 to allowing the water to be purified before reaching the dialyzer. If water source 110 contains premade dialysate, the dialysate added to fluid flow path 101 can be added downstream of sorbent cartridge 106 and directly pumped through dialyzer 103. If water source 110 contains purified water, the water source 110 can be either upstream or downstream of the sorbent cartridge 106, and the infusate system can be used to generate dialysate in-line by adding the components of the dialysate from infusate source 113, as described.

When the system is in multi-pass mode, or when water is used during single pass mode rather than pre-made dialysate, the dialysate can be regenerated by sorbent cartridge 106, and infusates added from infusate source 113 to regenerate the dialysate. Water can be added from water source 110 or a separate water source if necessary to dilute the dialysate. One or more sensors (not shown) can be included in fluid flow path 101 to ensure that the dialysate entering dialyzer 103 has the proper concentrations of all solutes.

The larger the portion of therapy spent in single pass mode or in a mode of operation where water is added to the system, the higher the need for additional purified water. In certain embodiments, the system can be programmed to switch a mode of operation at a predetermined time to minimize the purified water requirements while ensuring that the patient can complete a dialysis session. The control system can be programmed to receive one or more patient parameters and system parameters and determine a time during a dialysis session to switch the mode of operation between either single pass and multi-pass mode, or by adjusting the water addition rate to add more or less water to the system. The control system can receive the patient and system parameters through any means. For example, a user interface can be provided for the user to enter the patient and system parameters. Alternatively, the control system can receive the patient and system parameters directly from electronic patient records, from a smart card or similar device associated with the patient or system components, or any other source. Generally, the system will begin in single pass mode and then switch to multi-pass mode at a predetermined time during the dialysis session. However, in certain embodiments, the system will begin in multi-pass mode and then switch to single pass mode at a predetermined time during the dialysis session.

Alternatively, the system can use continuous water addition, either profiled or constant during therapy. A predetermined water addition rate can be used to dilute the dialysate upstream of the sorbent cartridge throughout the entire therapy. The water addition rate can be constant, or changed during therapy. For example, the water addition rate can be set at the dialysate flow rate near the beginning of therapy, which would mean the system would be operating in single pass mode. Throughout therapy, the water addition rate can be lowered towards 0%, or purely multi-pass mode. In certain embodiments, even when operating in a single pass mode, a small amount of dialysate can still be passed through the sorbent cartridge, such as about 5%. Having 5% of spent dialysate go through the cartridge will acidify that portion of the dialysate and provide enough acid, so that when bicarbonate infusate is added, less or no additional acid will be needed to achieve the desired dialysate pH. Alternatively, the water addition rate can be set as some percentage of the dialysate flow rate. Water can be added upstream of the sorbent cartridge 106, and then removed downstream of the dialyzer. Continuously adding water upstream of the sorbent cartridge 106 and removing the added water results in a hybrid system that is not entirely single pass or multi-pass.

Alternatively, a sensor 116 can be included in the fluid flow path 101 that can be used to monitor a dialysis session status and switch when a predetermined clearance level is reached. For example, a urea, creatinine or other sensor 116 between dialyzer outlet 105 and valve 107 in FIG. 1 could detect when the patient has reached a desired percent of clearance in the session. The control system can be programmed to switch mode of operation when a predetermined percent of clearance has been reached. An optional sensor 118 downstream of sorbent cartridge 106 can also be included. Sensor 118 can be used to determine if the functional capacity of the sorbent cartridge 106 is exceeded. Sensor 118 can be an ammonia sensor to determine if the adsorptive capacity of the zirconium phosphate has been exceeded. Alternatively, sensor 118 can be a pH sensor to determine if the buffering capacity of zirconium phosphate has been reached. If the capacity of the zirconium phosphate is reached, the system can be switched into a single-pass mode.

The length of the portion of a dialysis session that can be spent in multi-pass mode, or with a low water addition rate, is a function of the capacity of the sorbent cartridge used and the amount of solutes that are adsorbed by the sorbent cartridge. Zirconium phosphate or a cation exchange resin adsorbs cations such as potassium, calcium, magnesium, and ammonium ions generated from the breakdown of urea. Zirconium oxide adsorbs anions such as phosphate and fluoride anions. Activated carbon adsorbs creatinine, uric acid, proteins and other toxins. Patient weight, patient pre-dialysis BUN level, patient volume and patient pre-dialysis levels of other solutes adsorbed by the sorbent material can all influence the point at which the capacity of the sorbent cartridge will be exceeded. Further, the urease activity level can limit the conversion of urea depending on the concentration of urea in the dialysate. If the urea level is too high at the start of a treatment, the urea may not be sufficiently converted by the urease. Therefore, starting in single-pass mode, or multi-pass mode with high water dilution may be needed until the urea level has decreased to a level that the urease can sufficiently convert. Similarly, dialysis parameters, such as the bicarbonate prescription, blood flow rate, dialysate flow rate, patient bicarbonate level, and dialyzer koA can influence the point at which the capacity of the sorbent cartridge will be exceeded.

Table 1 shows a non-limiting embodiment of input patient and system parameters to determine a time during a dialysis session to switch from single pass mode to multi-pass mode for seven different hypothetical patients, in order to not exceed the urea capacity of the sorbent cartridge. The output, including the amount of time required for single pass mode is shown in Table 2 calculated using the below formula. $tsp=t-W\times0.6\times[Co-C0(1-URR)]/t$ where tsp is single pass time, t total session time, W patient weight, C0 patient urea level at the start. this equation assumes a linear urea removal rate over time and approximate water weight to be 60% of body weight.

TABLE 1

| | | Input | | | |
|---|---|---|---|---|---|
| | Desired URR | Pre-Dialysis BUN | Duration of Therapy | Patient Weight | Urea Capacity of Sorbent Cartridge |
| Patient A | 0.70 | 30.00 mM | 4.00 hr | 110.00 kg | 1193.00 mmol |
| Patient B | 0.70 | 30.00 mM | 4.00 hr | 148.00 kg | 1193.00 mmol |
| Patient C | 0.70 | 30.00 mM | 4.00 hr | 115.00 kg | 1193.00 mmol |
| Patient D | 0.70 | 30.00 mM | 4.00 hr | 120.00 kg | 1193.00 mmol |
| Patient E | 0.70 | 30.00 mM | 4.00 hr | 125.00 kg | 1193.00 mmol |
| Patient F | 0.70 | 30.00 mM | 4.00 hr | 130.00 kg | 1193.00 mmol |
| Patient G | 0.70 | 30.00 mM | 4.00 hr | 140.00 kg | 1193.00 mmol |

TABLE 2

| | | Output | | | |
|---|---|---|---|---|---|
| | Post-Dialysis BUN | Total Urea Removed | Rate of Urea Removal (mmol/hr) | Sing Pass Treatment | Water Required |
| Patient A | 9.00 mM | 1386.00 mmol | 346.50 | 0.56 hr | 16.71 L |
| Patient B | 9.00 mM | 1864.80 mmol | 466.20 | 1.44 hr | 42.23 L |
| Patient C | 9.00 mM | 1449.00 mmol | 362.25 | 0.71 hr | 21.20 L |
| Patient D | 9.00 mM | 1512.00 mmol | 378.00 | 0.84 hr | 25.32 L |
| Patient E | 9.00 mM | 1575.00 mmol | 393.75 | 0.97 hr | 29.10 L |
| Patient F | 9.00 mM | 1638.00 mmol | 409.50 | 1.09 hr | 32.60 L |
| Patient G | 9.00 mM | 1764.00 mmol | 441.00 | 1.29 hr | 38.84 L |

The patients in Tables 1 and 2 are each using identical sorbent cartridges having a total urea capacity of 1193.00 mmol, assuming that the zirconium phosphate can remove 0.9 mmol of ammonium ions per gram and 2.65 kg of zirconium phosphate. All patients begin with a pre-dialysis BUN level of 30.00 mM, and have a target urea reduction ratio (URR) of 0.70 over a four-hour dialysis session. The only difference between the patients is the patient weight, which varies from 110.00 kg for patient A up to 148.00 kg for patient B.

The post dialysis BUN level for each patient is given by Eq (1), where $BUN_{pre}$ is the pre dialysis BUN level and $BUN_{pre}$ is the post dialysis BUN level.

$$BUN_{post}=BUN_{pre}*(1-URR) \qquad Eq(1)$$

With a URR of 0.70 and a pre-dialysis BUN level of 30.00 mM, the post dialysis BUN level for each patient is 9.00 mM. Assuming that 60% of the patient weight is water, the total urea removed for each patient is given by Eq (2), where $Urea_{rem}$ is the amount of urea removed and W is the patient weight.

$$Urea_{rem}=W*0.6*(BUN_{pre}-BUN_{post}) \qquad Eq(2)$$

As shown in Table 2, with the given patient weights, 1386.00 mmol of urea is removed from patient A, while 1864.80 mmol of urea is removed from patient B. The amount of urea removed from each of patients C-G varies between the two extremes of patients A and B directly in proportion to the starting patient weight. The total urea removed divided by the duration of therapy provides the rate of urea removal throughout the dialysis session. In certain embodiments, the blood flow rate can be increased while the system is operating in single-pass mode, which may increase clearance during single-pass mode. Increasing clearance while operating in single pass mode would make the sorbent cartridge more efficient when operating in multi-pass mode. The length of time necessary to use single pass mode is given by Eq (3), where $T_s$ is the length of time for single pass mode, D is the duration of the dialysis session, C is the urea capacity of the sorbent cartridge, and R is the rate of urea removal.

$$T_s=D-(C/R) \qquad Eq(3)$$

The total volume of water required for treatment depends on the length of time spent in single pass mode, and is given by Eq (4), where V is the water required.

$$V=(T_{s/D})*120 \qquad Eq(4)$$

As shown in Tables 1 and 2, patient A can achieve the desired URR given the system and patient parameters if 0.56 hrs of the treatment is spent in single pass mode. As such, the control system can cause the system to switch from single pass mode to multi-pass mode 0.56 hrs into the dialysis session for patient A. Alternatively, the system can start in multi-pass mode and control system can switch from multi-pass mode to single pass mode 3.44 hrs into the dialysis session. For patient B, 1.44 hrs of single pass treatment is required. As such, the control system can cause the system to switch from single pass mode to multi-pass mode 1.44 hrs into the dialysis session. Alternatively, the system can start in multi-pass mode and control system can switch from multi-pass mode to single pass mode 2.56 hrs into the dialysis session. Similarly, patient C requires 0.71 hrs of single pass mode; patient D requires 0.84 hrs of single pass mode; patient E requires 0.97 hrs of single pass mode; patient F requires 1.09 hrs of single pass mode; and patient G requires 1.29 hrs of single pass mode.

Eq's (1-4) assume a constant rate of removal of uremic toxins. However, the actual concentration of uremic toxins in the dialysate may be reduced by exponential decay. The expected exponential decay of urea (or any other uremic toxin) during a therapy, will determine a smaller volume of single pass volume to be needed. The time on single-pass mode (t-sp) using exponential decay can be given by Eq (5).

$$t\text{-}sp=-(V/D)*\ln[(Ms/A)+e\hat{\ }(-D*t/V)] \qquad EQ (5)$$

where V is the patient volume, D is the dialysance (which depends on dialyzer koA, dialysate flow rate and blood flow rate), Ms is the capacity of the sorbent to remove a uremic toxin, t is the total session time, and A is provided by EQ (6)

$$A=(Qd-Qc-Qw)*(V/D)*Cpo \qquad EQ (6)$$

Where Qd is dialysate flow rate, Qc is the flow rate of infusates added after the sorbent cartridge, and Qw is the water dilution rate used during multi-pass, and Cpo is the patient starting level for the uremic toxin of interest. For example, using patient A from the table above and using the t-sp equation with Qd=0.6-L/min and a required dialysance (D) of 0.331-L/min to achieve a URR of 0.70, and a Qw of 0.00-L/min during multi-pass, a single-pass water volume of 11.96-L is needed, or 0.33-hours in single-pass mode, which is less than the amount of water needed using the constant removal equations summarized in Table 2.

Figure 2:
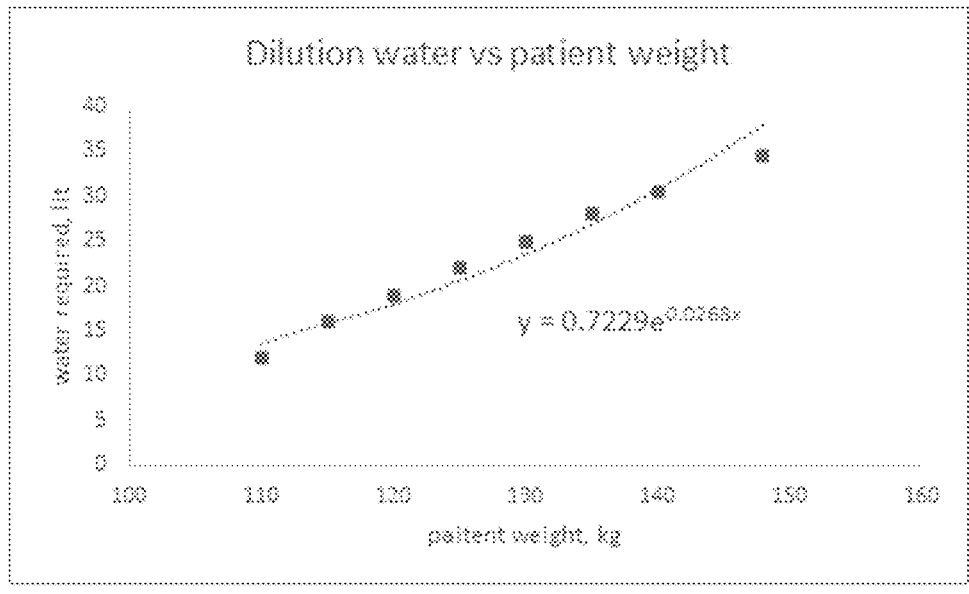
FIG. 2 is a graph showing the amount of water required to treat a patient vs. patient weight.

FIG. 2 is a graph showing the amount of water required for effective treatment vs. patient weight using the input parameters from Table 1 and the exponential decay equations. As illustrated in FIG. 2, the amount of water required is directly proportional to patient weight, as the amount of water required is a function of the amount of time spent in single pass mode. Heavier patients require more urea removal, reach the sorbent cartridge capacity faster, and therefore require longer single pass treatment to achieve the desired urea reduction ratio. Although described as relating to urea removal, the same equations can be used based on any uremic toxin.

Figure 5:
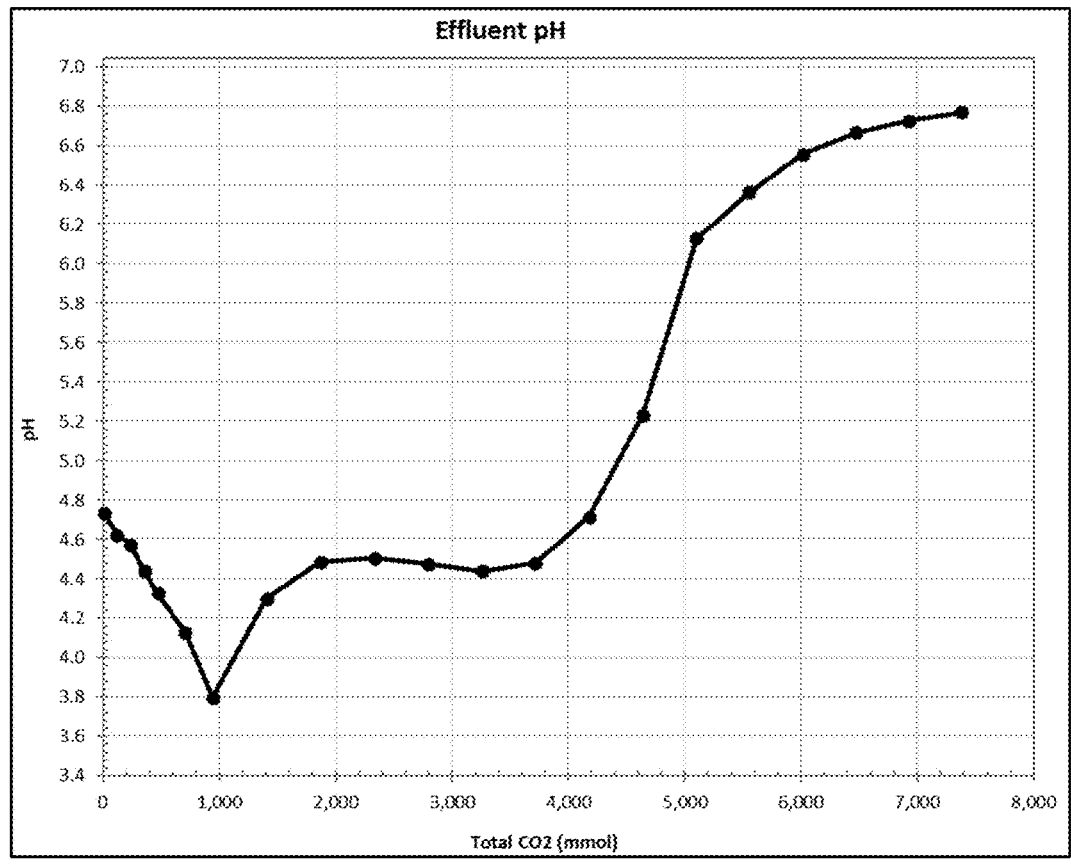
FIG. 5 is a graph showing the sorbent cartridge effluent pH as a function of total $CO_2$ passed through the sorbent cartridge.

In cases where the titration of the zirconium phosphate is to be avoided, in order to maintain better bicarbonate control during multi-pass mode, the time on single-pass mode can be determined. The titration of zirconium phosphate occurs with exposure to bicarbonate. Bicarbonate sources come from the break down of urea to ammonium carbonate, bicarbonate present in the dialysate and bicarbonate present in the patient. Similar to urea capacity, related to ammonium removal by the zirconium phosphate, the zirconium phosphate will also have a capacity to total bicarbonate exposure before the pH starts to rise above some critical value. For improved bicarbonate control, in certain embodiments, the effluent zirconium phosphate pH may be kept below 5, so the bicarbonate leaving the sorbent cartridge is in $CO_2$ form, which can be removed by degassing out of the dialysate. FIG. 5 shows a typical titration curve for a sorbent cartridge using zirconium phosphate with a slurry pH of 3. The total bicarbonate (Total $CO_2$ on the x-axis) exposure is 4500-mmol before the pH starts to rise above 5. An equation to determine the mass exposure to the sorbent cartridge based on mass balances across the patient, dialyzer and dialysate flow path is given as EQ (7):

$$Ms=(Qd-Qc-Qw)*Cd*t-Qw*Ca*t+(Qd-Qc-Qw)*$$
$$(V/Qd)*(Cpo-Cd)*[1-e^{\char`\^}(-D*t/V)] \qquad \text{EQ (7)}$$

Where Cd is the level in the dialysate entering the dialyzer, Ca is the concentration of acid in the dilution water, Qw is the water addition rate. Acid can be added to the dilution water to consume bicarbonate in the spent dialysate entering the sorbent cartridge. A strong acid such as hydrochloric acid can be used. Using the equations above for both urea and bicarbonate, the mass of total bicarbonate (urea+bicarbonate) can be determined that will be exposed to the sorbent cartridge. If the mass of total bicarbonate exceeds the capacity of the sorbent cartridge then a certain amount of time on single pass can be determined to avoid exceeding the capacity. For example, using Patient A in Table 1 and assuming a bicarbonate level of 40 mM in the dialysate, a starting bicarbonate level of 20 mM in the patient, a Ca level of 0, and a total bicarbonate capacity of 4500-mmol the time on single pass needed is 1-hour, or 36.4-Liters of single-pass dialysate to avoid exceeding capacity.

Another approach involves using a constant water dilution flow rate throughout multi-pass therapy to avoid exceeding the sorbent cartridge capacity. Using the same mass balance approach, EQ (8) is derived to determine the amount of water flow rate needed:

$$Qw=[(Cd1*t+A1+Cd2*t+A2)*(Qd-Qc)-M]/[Cd1*t+$$
$$A1+Cd2*t+A2+Ca*t] \qquad \text{EQ (8)}$$

Where Cd1 and Cd2 are the dialysate levels for species 1 and 2, and A is given by EQ (9):

$$A=(V/Qd)*(Cpoi-Cdi)*(1-e^{\char`\^}(-D*t/V)) \qquad \text{EQ (9)}$$

Where Cpoi is the starting patient level for species i and Cdi is the dialysate level for species i. Using the parameters for Patient A, and the values used in the previous paragraph, a Qw flow rate of 0.164-L/min is needed for a total volume of 39.3-liters. This approach is not as efficient as the single-pass followed be multi-pass, which only required 36.4-liters. Also, if the Ca level is 5 mM, the volume decreases to 35.2-liters from 39.3 liters due to the consumption of bicarbonate by the 5 mM of acid in the dilution water. Although the constant dilution method is not as efficient as single pass followed by multi-pass, for the example given, it does provide a more straightforward control method, since a fixed constant water dilution rate is used for the whole therapy.

As described, a control system in the dialysis system can be programmed to determine the time at which to switch mode of operation either between single pass and multi-pass mode, or by changing the water addition rate. Using the various patient parameters and Eq's (1)-(9), the process can determine the proper time to switch mode of operation and then control the system to switch at the predetermined time. One of skill of the art will understand how to determine the time to switch mode of operation based on different input values for patient weight, patient volume, pre-dialysis BUN level, desired URR, and sorbent cartridge capacity, and dialysate flow rate, infusate flow rates, and multi-pass water dilution flow rate. For example, a lesser amount of zirconium phosphate in the sorbent cartridge would result in a longer time spent in single pass mode or a higher water addition rate throughout therapy. Similarly, a higher desired URR or higher starting BUN level would also result in a longer time spent in single pass mode or a higher water addition rate. The control system can be programmed to update the values used for the variables in Eq's (1)-(9) with the specific input system and patient parameters to allow for full treatment of any patient.

Figure 3:
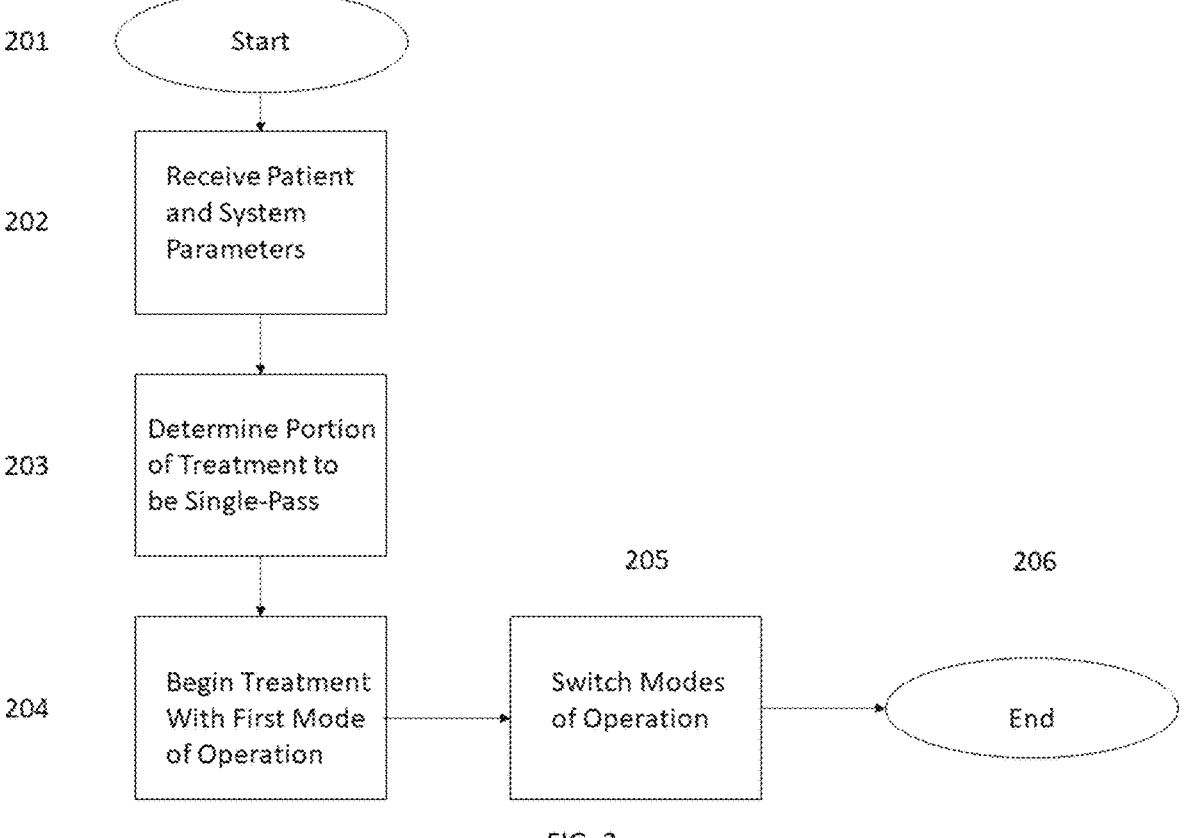
FIG. 3 is a flow chart showing a process of controlling a mode of operation of a dialysis system to improve the operational capabilities of the system.

FIG. 3 is a flow chart of the method for increasing the operational capabilities of a sorbent-based dialysis system. The method can start in step 201. In step 202, system and patient parameters can be obtained. As described, the predetermined time to switch between single pass mode and multi-pass mode is a function of patient parameters, such as patient weight, patient pre-dialysis BUN level, and a desired urea reduction ratio of the patient. The predetermined time can also depend on system parameters such as the length of time of the dialysis session and the sorbent cartridge capacity. Based on the patient and system parameters, the length of time of single pass mode can be determined using Eq's (1)-(3) in step 203. Based on the portion of the total treatment time to spend in single-pass mode, the control system can set a predetermined time to switch between single pass and multi-pass mode.

Treatment can begin in step 204. At the predetermined time, the system can switch modes of operation in step 205. As described, the system can start in single pass mode and switch to multi-pass mode at the predetermined time, or the system can start in multi-pass mode and switch to single-pass mode at the predetermined time. The dialysis session can continue after switching modes of operation until the dialysis session ends in step 206. Although described as switching from purely single pass mode to purely multi-pass mode in FIG. 3, one of skill in the art will understand that the same method can be used when controlling a water addition rate to be between 0 and 100%.

Figure 4A:
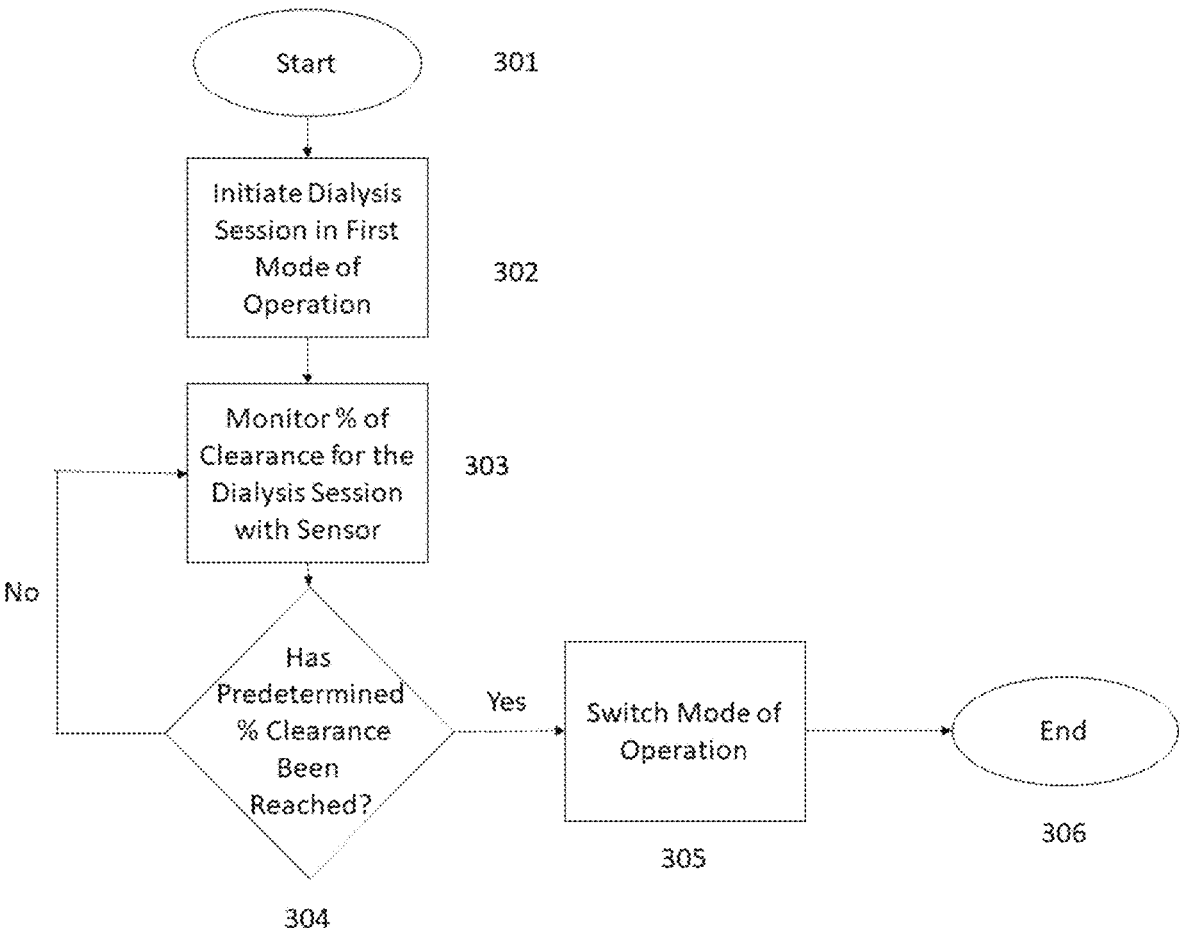
FIGS. 4A-4B are flow charts showing a process of controlling a mode of operation of a dialysis system based on one or more sensors.

FIG. 4A is a flow chart of the method for increasing the operational capabilities of a sorbent-based dialysis system using a sensor. The method can start in step 301. In step 302, a dialysis session can be initiated using a first mode of operation. As described, the first mode of operation can be a single pass mode, while the second mode of operation is a multi-pass mode. Alternatively, the first mode of operation can be a multi-pass mode, while the second mode of operation is a single pass mode. In step 303, the control system can monitor a percent clearance reached for the dialysis session. A sensor in communication with the control system can be used to determine the dialysate concentration of one or more solutes. The solutes can include creatinine, urea, or any other markers that will enable to control system to determine the percent clearance reached for the dialysis session. For example, a urea sensor can be used. When the urea concentration exiting the dialyzer has decreased by a predetermined amount, the control system can make a determination that the predetermined percent clearance for the dialysis session has been reached. In step 304, the control system can determine whether the dialysis session has reached a predetermined percent clearance. If not, the system can continue in the first mode of operation while monitoring the percent clearance for the dialysis session in step 303. Once the predetermined percent clearance for the dialysis session is reached, the control system can switch modes of operation in step 305. The dialysis session can continue after switching modes of operation until the dialysis session ends in step 306. Although described as switching from purely single pass mode to purely multi-pass mode in FIG. 4A, one of skill in the art will understand that the same method can be used when controlling a water addition rate to be between 0 and 100%. The % clearance used to determine when to switch mode of operation can be patient and treatment specific. For example, using a known patient weight and monthly BUN measurements, the expected urea removal can be calculated as described using EQ's (1)-(2). Knowing the sorbent cartridge capacity, one of skill in the art could calculate the fraction of removal that needs to be in single pass mode. Alternatively, if the patient's uremic status is unknown, one could set the fraction of single pass mode to be (patient weight–labeled max patient weight)/ Patient weight, and adjust up or down based on whether or not the treatment completes before reaching cartridge capacity.

In certain embodiments, the system can switch between single pass and multi-pass modes multiple times during a dialysis session. For example, certain conditions can cause an increase in dialysate concentration of one or more solutes during a dialysis session due to release of the ions from the sorbent cartridge. Temporarily switching to single pass mode can remove these ions from the dialysate to the drain. Once the dialysate concentration of the solutes reaches acceptable levels, the system can switch back into multi-pass mode. As described, one or more sensors can be included in the fluid flow path to determine the dialysate concentration of specific solutes. Further, if the sorbent cartridge capacity is exceeded during a dialysis session, the system can be switched into purely single pass mode to extend the therapy. An ammonia sensor positioned downstream of the sorbent cartridge can be used to determine when the sorbent capacity is reached. Ammonia detected downstream of the sorbent cartridge would indicate that the capacity of the zirconium phosphate is exceeded. Alternatively, a pH sensor can be included to determine if the zirconium phosphate buffering capacity is exceeded.

Figure 4B:
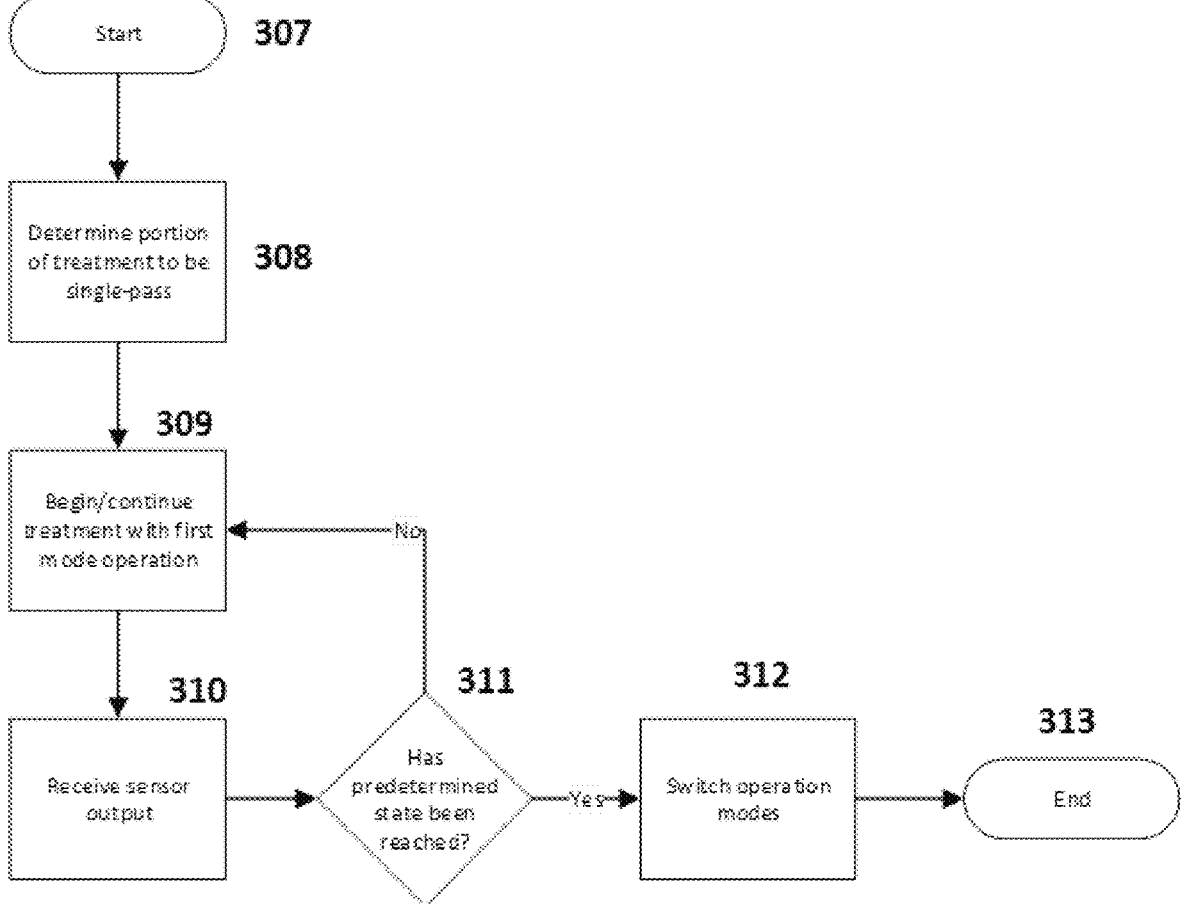

FIG. 4B is a flow chart of an alternative method for increasing the operational capabilities of a sorbent-based dialysis system using a sensor. The method can start in step 307. In step 308, a predetermined portion of a dialysis session in single-pass mode can be determined. For example, 50% of the total clearance expected for a dialysis session can be performed using single pass mode. The dialysis session can begin in step 309 using the first mode of operation. The control system can receive information from a sensor in the dialysis flow path in step 310. Based on the sensor, the system can determine what portion of the expected clearance has been reached. In step 311, the system can determine whether the predetermined portion of the dialysis session has been reached. If not, the method can continue with monitoring the dialysate to determine the portion of clearance reached in step 309. Once the predetermined portion of the dialysis session has been reached, the method can continue in step 312 with switching the mode of operation. The dialysis session can continue after switching modes of operation until the dialysis session ends in step 313. Although described as switching from purely single pass mode to purely multi-pass mode in FIG. 4B, one of skill in the art will understand that the same method can be used when controlling a water addition rate to be between 0 and 100%.

One skilled in the art will understand that various combinations and/or modifications and variations can be made in the described systems and methods depending upon the specific needs for operation. Various aspects disclosed herein may be combined in different combinations than the combinations specifically presented in the description and accompanying drawings. Moreover, features illustrated or described as being part of an aspect of the disclosure may be used in the aspect of the disclosure, either alone or in combination, or follow a preferred arrangement of one or more of the described elements. Depending on the example, certain acts or events of any of the processes or methods described herein may be performed in a different sequence, may be added, merged, or left out altogether (e.g., certain described acts or events may not be necessary to carry out the techniques). In addition, while certain aspects of this disclosure are described as performed by a single module or unit for purposes of clarity, the techniques of this disclosure may be performed by a combination of units or modules associated with, for example, a medical device.

What is claimed is:
1. A system comprising:
a fluid flow path comprising:
    a dialyzer outlet fluidly connectable to a dialyzer;
    a first valve fluidly connecting the fluid flow path to a drain line;
    a sorbent cartridge positioned downstream of the first valve;
    a second valve fluidly connecting the fluid flow path to a water source; and
    a dialyzer inlet downstream of the sorbent cartridge; and
a control system,
    wherein the control system is programmed to control a mode of operating the fluid flow path between a first mode of operation and a second mode of operation by controlling a water addition rate using the first valve and the second valve,
        wherein one of the first mode of operation and the second mode of operation is a hybrid mode,
            wherein, in the hybrid mode, at least a first portion of a fluid in the fluid flow path is diverted to the drain line and while the at least first portion of the fluid is diverted to the drain line, at least a second portion of the fluid simultaneously remains in the fluid flow path; and
    wherein the control system is programmed to temporarily switch the mode of operation during a dialysis session based on a detected condition of the fluid flow path, until the detected condition is resolved.
2. The system of claim 1, wherein the first mode of operation is a first water addition rate and the second mode of operation is a second water addition rate.

3. The system of claim 1, wherein the control system is programmed to switch from the first mode of operation to the second mode of operation at a predetermined time during the dialysis session.

4. The system of claim 3, wherein the control system is programmed to determine the predetermined time based on one or more patient parameters.

5. The system of claim 3, wherein the control system is programmed to determine the predetermined time based on a sorbent cartridge capacity.

6. The system of claim 3, wherein the predetermined time is based on a patient weight.

7. The system of claim 3, wherein the predetermined time is based on at least one of a patient BUN level, a bicarbonate prescription, blood flow rate, dialysate flow rate, dialyzer koA, and patient volume.

8. The system of claim 1, further comprising at least one sensor between the dialyzer outlet and the first valve.

9. The system of claim 8, wherein the control system is programmed to determine a percent clearance for a dialysis session based on the at least one sensor.

10. The system of claim 9, wherein the control system is programmed to switch the mode of operation at a predetermined percent clearance.

11. The system of claim 8, wherein the sensor measures either creatinine or urea.

12. The system of claim 8, wherein the control system is programmed to determine if a sorbent cartridge capacity has been reached based on the at least one sensor.

13. The system of claim 12, wherein the control system is programmed to switch from the hybrid mode to a single pass mode if the sorbent cartridge capacity has been reached.

14. The system of claim 1, wherein the detected condition is a concentration of one or more solutes in the dialysate due to release of the ions from a sorbent cartridge.

15. The system of claim 1, wherein the detected condition is ammonia detected by an ammonia sensor positioned downstream of a sorbent cartridge.

16. The system of claim 1, further comprising:

a sensor positioned fluidly between the dialyzer inlet and the sorbent cartridge configured to detect if at least one capacity of the sorbent cartridge has been reached.

17. The system of claim 1, wherein the first valve is a proportioning valve configured to divert between 0% to 100% of the flow through the first valve to the drain line based on the mode of operating the fluid flow path.

18. A system comprising:

a fluid flow path fluidly connected to a dialyzer comprising:

i) a first valve fluidly connecting the fluid flow path to a drain line; and ii) a second valve fluidly connecting the fluid flow path to a water source; and a control system, wherein the control system is programmed to control a mode of operating the fluid flow path between a plurality of modes of operation by controlling a water addition rate, wherein a first mode of the plurality of modes of operation is a single pass mode and a second mode of the plurality of modes of operation is a hybrid mode, wherein, in the single pass mode, all of a fluid that passes through the first valve is diverted to the drain line, wherein, in the hybrid mode, at least a first portion of a fluid in the fluid flow path is diverted to the drain line and while the at least first portion of the fluid is diverted to the drain line, at least a second portion of the fluid simultaneously remains in the fluid flow path, and water is pumped into the fluid flow path from the water source; and wherein the control system is programmed to switch the mode of operation during a dialysis session to the single pass mode when a concentration of solutes in the fluid is detected and is programmed to switch the mode of operation back to the hybrid mode when the concentration of solutes in the fluid reaches a threshold level.

* * * * *